United States Patent [19]
Gordon et al.

[11] Patent Number: 6,025,511
[45] Date of Patent: Feb. 15, 2000

[54] METHOD OF INHIBITING PARASITIC ACTIVITY

[75] Inventors: Jeffrey I. Gordon, Olivette; George W. Gokel, Chesterfield, both of Mo.; Paul T. Englund, Baltimore, Md.

[73] Assignees: Washington University, St. Louis, Mo.; Johns Hopkins University, Baltimore, Md.

[21] Appl. No.: 09/052,210

[22] Filed: Mar. 31, 1998

Related U.S. Application Data

[62] Division of application No. 08/617,246, Mar. 18, 1996, Pat. No. 5,760,259, which is a division of application No. 08/523,301, Sep. 5, 1995, Pat. No. 5,747,537.

[51] Int. Cl.$^7$ .................................................. C07C 53/00
[52] U.S. Cl. ........................ 554/220; 514/558; 514/559; 514/560
[58] Field of Search ............................ 584/85, 101, 213, 584/218, 220; 514/558, 589, 560, 516, 706, 715, 717

[56] References Cited

U.S. PATENT DOCUMENTS 5,151,445  9/1992  Welply et al. ............................ 514/557

OTHER PUBLICATIONS

Doring et al., Proc. Natl. Acad. Sci., vol. 91, pp. 9735–3739, Oct. 1994.
Gokel et al., Lsrael Journal of Chemisrty, vol. 32, pp. 127–133, 1992.
Kishore et al., Journal of Biological Chemistry, vol. 266, pp. 8835–8855, 1991.
Doering et al., Science 252, 1851–1854 (1991).
Low, Biochem. J. 244, 1–13 (1987).
Ferguson, Science 239, 753–759 (1988).
Ferguson & Cross, J. Biol. Chem. 259, 3011–3015 (1984).
Ferguson et al., Ibid. 260, 4963–4968 (1985).
Heuckeroth et al., J. Biol. Chem. 263, 2127–2133 (1988).
Heuckeroth et al., Proc. Natl. Acad. Sci. USA 85, 8795–8799 (1988).
Heuckeroth et al., Proc. Natl. Acad. Sci. USA 86, 5262–5266 (1989).
Bryant, et al., Proc. Natl. Acad. Sci. USA 86, 8655–8659 (1989).
Kishore et al., J. Biol. Chem. 266, 8835–8855 (1991).
Devadas et al., J. Biol. Chem. 267, 7224–7293 (1992).
Gokel et al., Israel J. Chem. 32, 127–133 (1992).
Rudnick et al., Proc. Natl. Acad. Sci. 89, 10507–10511 (1992).
Lu et al., J. Biol. Chem. 269, 5346–5357 (1994).

*Primary Examiner*—Deborah Carr
*Attorney, Agent, or Firm*—Scott J. Meyer

[57] ABSTRACT

A method of inhibiting parasitic activity is disclosed in which the biosynthesis, structure and/or function of the glycosyl phosphatidylinositol (GPI) anchor of said parasite may be affected by incorporating into said GPI anchor selected analogs of myristic acid containing various heteroatoms, substituents and unsaturated bonds, including ester-containing analogs, ketocarbonyl-containing analogs, sulfur-containing analogs, double bond- and triple bond-containing analogs, aromatic moiety-containing analogs, nitrated analogs and halogenated analogs.

1 Claim, 3 Drawing Sheets

METHOD OF INHIBITING PARASITIC ACTIVITY

This is a DIVISION of application Ser. No. 08/617,246, filed Mar. 18, 1996, now U.S. Pat. No. 5,760,259, which is a DIVISION of application Ser. No. 08/523,301, filed Sep. 5, 1995, now U.S. Pat. No. 5,747,537.

This invention was made in part with government support under grant numbers A121334, A127179, and A130188 awarded by the National Institutes of Health and by grants from the MacArthur Foundation and Monsanto Company. The government has certain rights in the invention.

BACKGROUND OF THE INVENTION

This invention relates to a method of inhibiting parasitic activity by inhibiting the biosynthesis of the glycosyl phosphatidylinositol (GPI) anchor of the parasite. More particularly, the invention relates to the inhibition of parasitic activity by contacting said parasite with selected analogs of myristic acid containing various heteroatoms, substituents and unsaturated bonds.

Glycosyl phosphatidylinositols (GPIs) anchors diverse proteins to the plasma membranes of organisms ranging from the yeasts to mammals. See, e.g., the review article by Low, *Biochem. J.* 244, 1–13 (1987). One of the most completely characterized GPI anchors is that of the variant surface glycoprotein (VSG) of the parasitic protozoan *Trypanosoma brucei*. See, e.g., the research article by Ferguson et al. *Science* 239, 753–759 (1988), for the complete primary structure of the GPI anchors of VSG variant 117, and the review of GPI biosynthesis in *T. brucei* by Englund, *Ann. Rev. Biochem.* 62, 121–138 (1993). This parasite, in common with other African trypanosomes, evades the mammalian immune system by antigenic variation in which individual genes encoding immunologically distinct VSGs form a dense surface coat. The VSG coat acts as a macromolecular diffusion barrier which protects the parasite from lytic host-serum components.

*Trypanosoma brucei* is a protozoan bloodstream parasite responsible for African sleeping sickness which has a devastating effect on human health and on livestock production. Consequently, methods of inhibiting the activity of this and related protozoan parasites would have significant importance to medical science and for the development of therapeutic intervention to parasitic diseases.

Recently, in U.S. Pat. No. 5,151,445, certain myristic acid analogs have been disclosed as useful for inhibiting the growth and viability of bloodstream trypanosome parasites having a GPI membrane anchor. These analogs are oxy-substituted fatty acid analogs of $C_{13}$ and $C_{14}$ fatty acids or alkyl esters thereof in which a methylene group normally in carbon position from 4 to 13 of said fatty acid is replaced with oxygen. See also Doering et al., *Science* 252, 1851–1854 (1991).

BRIEF DESCRIPTION OF THE INVENTION

In accordance with the present invention, a method is provided for inhibiting parasitic activity of a bloodstream trypanosome parasite which comprises contacting said parasite with a compound selected from a group of myristic acid analogs containing various heteroatoms, substituents and unsaturated bonds. For purposes of convenience, these 53 selected analogs are divided into the following sub-groups with their chemical formulas being shown.

Thiatetradecanoic Acids $CH_3$—S—$(CH_2)_{11}$—COOH
$CH_3$—$CH_2$—S—$(CH_2)_{10}$—COOH
$CH_3$—$(CH_2)_3$—S—$(CH_2)_8$—COOH
$CH_3$—$(CH_2)_4$—S—$(CH_2)_7$—COOH
$CH_3$—$(CH_2)_5$—S—$(CH_2)_6$—COOH
$CH_3$—$(CH_2)_6$—S—$(CH_2)_5$—COOH
$CH_3$—$(CH_2)_7$—S—$(CH_2)_4$—COOH
$CH_3$—$(CH_2)_8$—S—$(CH_2)_3$—COOH

Oxygen and Sulfur Containing Analogs $CH_3$—$CH_2$—S—$(CH_2)_2$—O—$(CH_2)_7$—COOH

Oxotetradecanoic Acids $CH_3$—CO—$(CH_2)_{11}$—COOH
$CH_3$—$(CH_2)_2$—CO—$(CH_2)_9$—COOH
$CH_3$—$(CH_2)_3$—CO—$(CH_2)_8$—COOH
$CH_3$—$(CH_2)_4$—CO—$(CH_2)_7$—COOH
$CH_3$—$(CH_2)_6$—CO—$(CH_2)_5$—COOH
$CH_3$—$(CH_2)_8$—CO—$(CH_2)_3$—COOH
$CH_3$—$(CH_2)_9$—CO—$(CH_2)_2$—COOH

Ester-containing Analogs $CH_3$—O—CO—$(CH_2)_{10}$—COOH
$CH_3$—$(CH_2)_2$—O—CO—$(CH_2)_8$—COOH
$CH_3$—$(CH_2)_3$—O—CO—$(CH_2)_7$—COOH
$CH_3$—$(CH_2)_5$—O—CO—$(CH_2)_5$—COOH
$CH_3$—$(CH_2)_6$—O—CO—$(CH_2)_4$—COOH
$CH_3$—$(CH_2)_7$—O—CO—$(CH_2)_3$—COOH
$CH_3$—$(CH_2)_8$—O—CO—$(CH_2)_2$—COOH

Nitroalkylcarboxylic Acids $O_2N$—$(CH_2)_{12}$—COOH
$O_2N$—$(CH_2)_{10}$—COOH

Halogenated Analogs

Br—$(CH_2)_{12}$—COOH
Br—$(CH_2)_{13}$—COOH

Tetradecenoic Acids $CH_3$—$CH_2$—CH=CH—$(CH_2)_9$—COOH
$CH_3$—$(CH_2)_5$—CH=CH—$(CH_2)_5$—COOH
$CH_3$—$(CH_2)_6$—CH=CH—$(CH_2)_4$—COOH

Tetradecadienoic Acids $CH_3$—$(CH_2)_4$—CH=CH—CH=CH—$(CH_2)_4$—COOH
$CH_3$—$(CH_2)_5$—CH=CH—CH=CH—$(CH_2)_3$—COOH

Tetradecynoic Acids

HC≡C—$(CH_2)_{11}$—COOH
$CH_3$—$(CH_2)_2$—C≡C—$(CH_2)_8$—COOH
$CH_3$—$(CH_2)_3$—C≡C—$(CH_2)_7$—COOH
$CH_3$—$(CH_2)_4$—C≡C—$(CH_2)_6$—COOH
$CH_3$—$(CH_2)_5$—C≡C—$(CH_2)_5$—COOH
$CH_3$—$(CH_2)_6$—C≡C—$(CH_2)_4$—COOH
$CH_3$—$(CH_2)_7$—C≡C—$(CH_2)_3$—COOH
$CH_3$—$(CH_2)_5$—C≡C—$(CH_2)_4$—COOH

Aromatic Moiety-containing Analogs

11 Carbon Equivalent Length $C_6H_5$—$(CH_2)_7$—COOH

13 Carbon Equivalent Length $C_6H_5$—$(CH_2)_9$—COOH
$CH_3$—$CH_2$—$C_6H_4$—$(CH_2)_7$—COOH $CH_3—(CH_2)_3—O—C_6H_4—(CH_2)_4—COOH$ 14 Carbon Equivalent Length $C_6H_5—(CH_2)_{10}—COOH$
$CH_3—(CH_2)_4—O—C_6H_4—(CH_2)_4—COOH$
$CH_3—(CH_2)_3—O—C_6H_4—CH=CH—(CH_2)_3—COOH$
$CH_3(CH_2)_4—O—C_6H_4—CH=CH—(CH_2)_2—COOH$ Hetero-aromatic Analogs $CH_3—(CH_2)_6$-furyl$—(CH_2)_3—COOH$
$CH_3—(CH_2)_5$-furyl$—(CH_2)_4—COOH$
$CH_3—(CH_2)_4$-furyl$—(CH_2)_5—COOH$
2-Furyl$—(CH_2)_{10}—COOH$
2-Thienyl$—(CH_2)_{10}—COOH$ The chemical structures of the fifteen preferred compounds in the foregoing sub-groups are shown in Table 1 below. These compounds are listed in the approximate order of their toxic effect upon trypanosomes in culture, with the most toxic compounds at the top of the list. For purposes of comparison, the structures of five representative oxy-myristic acid analogs (oxatetradecanoic acids) disclosed in U.S. Pat. No. 5,151,445, are also included in this list. These five oxy-myristic acid analogs are as follows:

11-oxatetradecanoic acid, abbrev. O-11
10-oxatetradecanoic acid, abbrev. O-10
8-oxatetradecanoic acid, abbrev. O-8
7-oxatetradecanoic acid, abbrev. O-7
5-oxatetradecanoic acid, abbrev. O-5 mean and standard deviation of quadruplicate assays. All compounds were tested at 10 $\mu$M. The 0.1% ethanol in control E, corresponding to the final concentration of solvent present in other assays, had no effect on growth. Brackets on the right of the graph indicate the efficacy group designations for this test. As described in Methods herein below, 11-oxatetradecanoic acid and ethanol controls are defined as the middle value of groups 1 and 3, respectively. Compound codes corresponded to the following structures: 21, $CH_3—(CH_2)_3—CO—(CH_2)_8—COOH$; 22, $CH_3—(CH_2)_7—NH—CO—(CH_2)_3—COOH$; 23, $CH_3—(CH_2)_5—COOH$; 24, ethanol; 25, $CH_3—(CH_2)_4—CO—(CH_2)_7—COOH$; 26, $CH_3—(CH_2)_{10}—CO—CH_2—COOH$; 27, $CH_3(CH_2)_2—O—(CH_2)_9COOH$ (11-oxatetradecanoic acid); 28, $CH_3—(CH_2)_8—CO—(CH_2)_3—COOH$; 29, $CH_3—(CH_2)_6—NH—CO—(CH_2)_4—COOH$; 30, $CH_3—CH_2—CO—(CH_2)_{10}—COOH$; 31, $CH_3—(CH_2)_5—CO—(CH_2)_6—COOH$; 32, $CH_3—(CH_2)_9—CO—(CH_2)_2—COOH$; 33, $CH_3—(CH_2)_2—CO—(CH_2)_9—COOH$; 34, $CH_3—(CH_2)_8—NH—CO—(CH_2)_2—COOH$; 35, $CH_3—CO—(CH_2)_{11}—COOH$; 36, $CH_3—(CH_2)_7—CO—(CH_2)_4—COOH$.

Most of the myristic acid analogs used in the method of the present invention are well-known compounds which have been previously described as useful antiviral agents. See, e.g., Bryant et al., *Proc. Natl. Acad. Sci. USA* 86, 8655–8659 (1989), and Bryant et al., *Ibid.* 88, 2055–2059

TABLE 1

| Activity order | Compound Structure | systematic name |
|---|---|---|
| 1 | $CH_3(CH_2)_3C\equiv C(CH_2)_7COOH$ | 9-tetradecynoic acid |
| 2 | $CH_3(CH_2)_6—O—(CH_2)_5COOH$ | 7-oxatetradecanoic acid |
| 3 | $CH_3(CH_2)_6—CO—(CH_2)_5COOH$ | 7-oxotetradecanoic acid |
| 4 | $CH_3(CH_2)_6—S—(CH_2)_5COOH$ | 7-thiatetradecanoic acid |
| 5 | $CH_3(CH_2)_8—S—(CH_2)_3COOH$ | 5-thiatetradecanoic acid |
| 6 | $CH_3(CH_2)_7—O—CO—(CH_2)_3COOH$ | mono-n-octyl glutarate |
| 7 | $CH_3(CH_2)_5—CH=CH—CH=CH—(CH_2)_3COOH$ | 5,7-tetradecadienoic acid |
| 8 | $CH_3(CH_2)_4C\equiv C(CH_2)_6COOH$ | 8-tetradecynoic acid |
| 9 | $CH_3(CH_2)_3—O-p-C_6H_4—(CH_2)_4COOH$ | 5-(p-butoxyphenyl)pentanoic acid |
| 10 | $CH_3(CH_2)_5-2,5-C_4H_2O—(CH_2)_4COOH$ | 5-[2-(5-n-hexylfuryl)]pentanoic acid |
| 11 | $O_2N—(CH_2)_{12}COOH$ | 13-nitrotridecanoic acid |
| 12 | $CH_3(CH_2)_4—O-p-C_6H_4—(CH_2)_4COOH$ | 5-(p-pentoxyphenyl)pentanoic acid |
| 13 | $CH_3(CH_2)_2—O—(CH_2)_9COOH$ | 11-oxatetradecanoic acid |
| 14 | $CH_3(CH_2)_3—O—(CH_2)_8COOH$ | 10-oxatetradecanoic acid |
| 15 | $CH_3(CH_2)_8—O—(CH_2)_3COOH$ | 5-oxatetradecanoic acid |
| 16 | $CH_3—S—(CH_2)_{11}COOH$ | 13-thiatetradecanoic acid |
| 17 | $CH_3(CH_2)_5—O—(CH_2)_6COOH$ | 8-oxatetradecanoic acid |
| 18 | $CH_3(CH_2)_8—O—CO—(CH_2)_2COOH$ | mono-n-nonyl succinate |
| 19 | $CH_3(CH_2)_6—CO—(CH_2)_3COOH$ | 5-oxotetradecanoic acid |
| 20 | $CH_3(CH_2)_4—S—(CH_2)_7COOH$ | 9-thiatetradecanoic acid |

DETAILED DESCRIPTION OF THE INVENTION

While the specification concludes with claims particularly pointing out and distinctly claiming the subject matter regarded as forming the present invention, it is believed that the invention will be better understood from the following detailed description taken in conjunction with the accompanying drawings in which briefly:

BRIEF DESCRIPTION OF THE DRAWINGS

FIG. 1 is a bar graph which shows: Assay of analog toxicity. The toxicity of 16 compounds, identified only by code number was assessed relative to 11-oxatetradecanoic acid (0-11) and ethanol (E) controls. Each bar shows the (1991). In their activity as antiparasitic agents in the present invention, these myristic analogs function in a different manner than as antiviral agents. In their antiviral activity, these compounds serve as substrates of myristoyl CoA:protein N-myristoyltransferase, an enzyme which transfers myristate from myristoyl CoA to the amino terminal glycine residue of eukaryotic cellular and viral protein. In their antiparasitic activity, these compounds are incorporated into the GPI anchor of the parasite. However, the antiparasitic activity may also be mediated, in part, by alteration of N-myristoylated proteins, or by some change in membrane structure caused by incorporation of the myristic acid analog into phospholipids.

The syntheses of the myristic acid analogs used in the method of the present invention also are well-known. Thus, the synthesis of sulfur-containing myristic acid analogs is described, e.g., by Heuckeroth et al., *J. Biol. Chem.* 263, 2127–2133 (1988), Heuckeroth et al., *Proc. Natl. Acad. Sci. USA* 85, 8795–8799 (1988), and in U.S. Pat. Nos. 5,073,571 and 5,082,967. Double bond- and triple bond-containing myristic acid analogs are also described in said patents, in Heuckeroth et al., *Proc. Natl. Acad. Sci. USA* 85, 8795–8799 (1988), and in Rudnick et al., *Proc. Natl. Acad. Sci. USA* 89, 10507–10511 (1992). Synthesis of azido-substituted myristic acid analogs is described in EP 480,901. The preparation of many of these and other such myristic acid analogs containing oxygen, sulfur, double bond, triple bond and aromatic residues is described in Kishore et al., *J. Biol. Chem.* 266, 8835–8855 (1991). Synthesis of myristic acid analogs containing carbonyl groups, nitrogen heteroatoms and nitrogen heterocycles is described in Devadas et al., *J. Biol. Chem.* 267, 7224–7239 (1992). The synthesis of still other such triple bond- and aromatic moiety-containing analogs of myristic acid is described by Gokel et al., *Israel J. Chem.* 32, 127–133 (1992). Examples 1–43, below, illustrate the synthesis of 40 additional test compounds.

In order to illustrate the invention in greater detail, a total of 247 different myristic acid analogs (listed in Table 2, below) were tested for toxicity to trypanosomes in culture in accordance with a state-of-the-art assay. For comparison the testing included five oxy-myristic acid analogs (oxatetradecanoic acids) described in U.S. Pat. No. 5,151,445, the disclosure of which is incorporated herein by reference. Based on the test results, these 247 compounds were divided into three efficacy groups in which groups 2 and 3 consisted of the 60 active compounds whereas the 177 compounds of group 1 were inactive. Of the active compounds, the 20 compounds in group 3 were the most active. Although specific examples of the invention are thus illustrated herein, it will be understood that the invention is not limited to these specific examples or the details described therein. References to show the state-of-the-art are indicated in parentheses and appended at the end.

EXAMPLES

Materials and Methods

Materials—Fetal calf serum, hypoxanthine, MEM "alpha" medium (320-2561 AJ), penicillin, pyruvate, streptomycin and thymidine were obtained from Gibco/BRL. Other reagents, where not specified, were from Sigma Chemical Co.

Synthesis of fatty acid analogs. The methods used for synthesizing 203 of the 247 fatty acids shown in Table 1 are described in published reports (Rapaport and Newman, 1947; Kishore et al., 1991; Devadas et al., 1992; Gokel et al., 1992; Rudnick et al., 1992; footnote 3). The methods used to synthesize 40 additional fatty acids included in the panel are described below.

Chemical Analysis. Melting points were measured on a Laboratory Devices MEL-TEMP apparatus in open capillaries and are uncorrected. $^1$H-NMR spectra were recorded on a Hitachi Perkin-Elmer R-600 high resolution NMR spectrometer and on a Varian VXR 400 superconducting NMR. Spectra were obtained in CDCl$_3$ and are reported in ppm (δ) downfield from internal Me$_4$Si. IR spectra were recorded on a Perkin-Elmer Model 298 or 599 infrared spectrophotometer. TLC analyses were performed on silica gel 60F-254 plates (thickness=0.20 mm; Merck). Column chromatography was carried out with Merck Kieselgel 60 (70–230 mesh). Combustion analyses were conducted by Atlantic Microlab Inc., Atlanta, Ga. High resolution mass spectrometry was conducted at the Southern California Mass Spectrometer Facility, Department of Chemistry, University of California, Riverside. The CI/NH$_3$ experiments did not typically show MH+ ions so high resolution mass spectrometry was done on MNH$_4^+$ ions.

General procedure for Wittig reaction. Phosphonium bromide was treated with potassium t-butoxide in tetrahydrofuran (THF) under nitrogen with stirring for 30 min. The solution was cooled with ice. Aldehyde in THF was added dropwise, and the mixture was stirred for 12 h. The mixture was poured into water (150 mL), washed with Et$_2$O (50 mL), acidified (pH=1, 2N HCl) and extracted (hexanes, 4×50 mL), dried over MgSO$_4$, and the solvent was removed in vacuo. Chromatography (silica gel, 1:1 hexanes-ethyl acetate) and crystallization or Kugelrohr distillation yielded the product.

General procedure for hydrolysis reaction. A nitrile or ester containing compound, sodium hydroxide H$_2$O (20 mL), and EtOH (20 mL) were mixed and refluxed for 16 h. The mixture was cooled to room temperature, acidified (pH=1, 2N HCl), and extracted with ethyl acetate (4×50 mL). The organic solution was washed with water (2×50 mL), dried over MgSO$_4$ and evaporated. The residue was crystallized or distilled to afford the product.

General Procedure for hydrogenation reaction An unsaturated compound, 5% Pd/C or Pd/BaSO$_4$ and anhydrous EtOH (50 mL) were shaken under 15 psi H$_2$ for 1.0–4.0 h. The catalyst was filtered and washed with EtOH (2×15 mL). The solvent was evaporated in vacuo. The residue was crystallized or Kugelrohr distilled to afford the product.

TETRADECANDIENOIC ACIDS

Example 1

8,10-Tetradecandienoic acid.

This compound was synthesized from 7-carboxyheptyltriphenylphosphonium bromide (9.71 g, 20 mmol) and 2-trans-hexenal (1.96 g, 20 mmol) in 10% hexamethylphosphoric triamide (HMPA)-THF (100 mL) by a Wittig reaction. Kugelrohr distillation yielded the product (1.97 g, 44%) as a yellow oil (bp 123–126° C./0.01 torr). IR: 3450-2500, 1720 cm$^{-1}$; $^1$H-NMR: 0.95 (t, 3H), 1.35 (m, 8H), 1.62 m, 2H), 2.05 (m, 4H), 2.32 (t, 2H), 5.23 (m, 1H), 5.60 (m, 1H), 5.90 (m, 1H), 6.05 (m, 1H), 10.50 (bs, 1H). Anal. Calcd. for $C_{14}H_{24}O_2$: C, 74.95, H, 10.78%; Found: C, 75.01, H, 10.80%.

Example 2

6,8-Tetradecanedienoic acid.

This compound was synthesized from 5-carboxypentyltriphenylphosphonium bromide (9.50 g, 20 mmol) and 2-trans-octenal (2.52 g, 20 mmol) in 10% HMPA-THF (100 mL) by Wittig reaction. Kugelrohr distillation yielded the product (1.91 g, 43%) as a pale yellow oil (bp 122–125° C./0.01 torr). IR: 3500-2500, 1730 cm$^{-1}$; $^1$H-NMR: 0.95 (t, 3H), 1.40 (m, 10H), 2.30 (m, 6H), 6.00 (m, 4H), 11.30 (bs, 1H). Anal. Calcd. for $C_{14}H_{24}O_2$: C, 74.95, H, 10.78%; Found: C, 75.04, H, 10.80%.

Example 3

5,7-Tetracanedienoic acid.

This compound was synthesized from 4-carboxybutyltriphenylphosphonium bromide (8.87 g, 20 mmol) and 2-trans-nonenal (2.80 g, 20 mmol) in 10%

HMPA-THF (100 mL) by a Wittig reaction. Kugelrohr distillation afforded the product (1.96 g, 44%) as a pale yellow oil (bp 116–119° C./0.01 torr). IR: 3500-2500, 1730 cm$^{-1}$; $^1$H-NMR: 0.90 (t, 3H), 1.35 (m, 10H), 2.30 (m, 6H), 5.90 (m, 4H), 10.05 (bs, 1H). Anal. Calcd. for $C_{14}H_{24}O_2$: C, 74.95, H, 10.78%; Found: C, 74.87, H, 10.79%.

AROMATIC ANALOGS

Example 4

8-Phenoxyoctanoic acid.

Phenol (1.88 g, 20 mmol) was mixed with NaOH (0.80 g, 20 mmol) in EtOH (50 mL). 8-Bromooctanoic acid (2.23 g, 10 mmol) was then added to the mixture and refluxed for 12 h. After cooling to room temperature, water (100 mL) was added and the mixture was acidified with 2N HCl (pH=2). The solid was filtered and washed with water (2×50 mL), and recrystallized from hexane-ethyl acetate (5:1) to give the product as white brick-like crystals (1.79 g, 76%), mp 67–68° C.; $^1$H-NMR: 1.42 (m, 6H), 1.65 (m, 2H), 1.80 (m, 2H), 2.37 (t, 2H), 3.97 (t, 2H), 6.93 (m, 3H), 7.30 (t, 2H), 10.05 (bs, 1H). Anal. Calcd. for $C_{14}H_{20}O_3$: C, 71.16, H, 8.53%; Found: C, 71.09, H, 8.54%.

Example 5

8-(p-Methoxyphenyl)-7-octennitrile.

This compound was synthesized from 6-cyanohexyltriphenylphosphonium bromide (9.05 g, 20 mmol) and p-anisaldehyde (2.72 g, 20 mmol) in THF (100 mL) by a Wittig reaction. Kugelrohr distillation afforded the products (3.26 g, 71%) as a colorless liquid (bp: 143–146° C./0.05 torr). IR: 2285 cm$^{-1}$; $^1$H-NMR: 1.50 (m, 6H), 2.30 (m, 4H), 3.80 (s, 3H), 5.50 (m, 1H), 6.30 (d, 1H), 7.05 (q, 4H).

Example 6

8-(p-Methoxyphenyl)-7-octenoic acid.

This compound was synthesized from 8-(p-methoxyphenyl)-7-octennitrile (3.34 g, 15 mmol) by a hydrolysis reaction. Crystallization (hexanes-ethyl acetate) yielded the product (3.29 g, 88%) as white crystals (mp 42–43° C.). IR: 3400-2500, 1730 cm$^{-1}$; $^1$H-NMR: 1.50 (m, 6H), 2.35 (m, 4H), 3.82 (s, 3H), 5.55 (m, 1H), 6.35 (d, 1H), 7.05 (q, 4H), 11.20 (bs, 1H). Anal. Calcd. for $C_{15}H_{20}O_2$: C, 72.55, H, 8,12% Found: C, 72.41, H, 8.07%, Z:E=67:33.

Example 7

8-(p-Methoxyphenyl)octanoic acid.

This compound was synthesized from 8-(p-methoxyphenyl)-7-octenoic acid (1.24 g, 5 mmol) and Pd/BaSO$_4$ (125 mg) by hydrogenation. Crystallization (petroleum ether) afforded the product (1.20 g, 96%) as white crystals (mp 42–43° C.). IR: 3400-2500, 1705 cm$^{-1}$; $^1$H-NMR: 1.40 (m, 10H), 2.40 (m, 4H), 3.80 (s, 3H), 6.95 (q, 4H), 10.10 (bs, 1H). Anal. Calcd. for $C_{15}H_2O_2$: C, 71.97, H, 8.86%; Found: C, 72.07, H, 8.88%.

Example 8

7-(p-Ethoxyphenyl)-6-heptenoic acid.

This compound was synthesized from 5-carboxypentyltriphenylphosphonium bromide (9.50 g, 20 mmol) and p-ethoxybenzaldehyde (3.00 g, 20 mmol) in THF (100 mL) by a Wittig reaction. Crystallization (hexanes-ethyl acetate) afforded the product (3.18 g, 64%) as white crystals (mp 62–63° C.), IR: 3450-2500, 1720 cm$^{-1}$; $^1$H-NMR: 1.40 (t, 3H), 1.50 (m, 2H), 1.70 (m, 2H), 2.38 (m, 4H), 4.00 (q, 2H), 5.72+6.05 (m, 1H), 6.32 (t, 1H), 7.05 (q, 4H), 10.10 (bs, 1H). Anal. Calcd. for $C_{15}H_{20}O_3$: C, 72.55, H, 8.12% Found: C, 72.53, H, 8.15%. Z:E=45:55.

Example 9

7-(p-Ethoxyphenyl)heptanoic acid.

This compound was synthesized from 7-(p-ethoxyphenyl)-6-heptenoic acid (1.24 g, 5 mmol) and Pd/C (125 mg) by a hydrogenation reaction. Crystallization (petroleum ether) afforded the product (1.21 g, 97%) as white crystals (mp 65–66° C.). IR: 3400-2500, 1715 cm$^{-1}$; $^1$H-NMR: 1.32 (m, 7H), 1.55 (m, 5H), 2.30 (t, 2H), 2.50 (t, 2H), 3.95 (q, 2H), 6.90 (q, 2H), 10.20 (bs, 1H). Anal. Calcd. for $C_{15}H_{22}O_3$: C, 71.97, H, 8.86%; Found: C, 71.91, H, 8.87%.

Example 10

6-(p-Propoxyphenyl)-5-hexenoic acid.

This compound was synthesized from 4-carboxybutyltriphenylphosphonium bromide (8.87 g, 20 mmol) and p-propoxybenzaldehyde (3.28 g, 20 mmol, synthesized from p-hydroxybenzaldehyde and 1-iodopropane) in THF (100 mL) by a Wittig reaction. Crystallization (petroleum ether) afforded the product (3.75 g, 76%) as white crystals (mp, 49–50° C.). IR: 3400-2500, 1725 cm$^{-1}$; $^1$H-NMR: 1.00 (t, 3H), 1.75 (m, 4H), 2.35 (m, 4H), 3.90 (t, 2H), 5.55 (m, 1H), 6.35 (m, 1H), 7.00 (q, 4H), 11.30 (bs, 1H). Anal. Calcd. for $C_{15}H_{20}O_3$: C, 72.55, H, 8.12%; Found: C, 72.45, H, 8.13%. Z:E=35:65.

Example 11

6-(p-Propoxyphenyl)hexanoic acid.

This compound was synthesized from 6-(p-propoxyphenyl)-5-hexenoic acid (1.49 g, 6 mmol) and Pd/BaSO$_4$ (150 mg) by a hydrogenation reaction. Crystallization (petroleum ether) yielded the product (1.38 g, 92%) as white crystals (mp 42–43° C.), IR: 3400-2500, 1715 cm$^{-1}$; $^1$H-NMR: 1.00 (t, 3H), 1.55 (m, 8H), 2.40 (m, 4H), 3.90 (t, 2H), 6.95 (q, 4H), 7.90 (bs, 1H). Anal. Calcd. for $C_{15}H_{22}O_3$: C, 71.97, H, 8.86%; Found: C, 72.04, H, 8.88%.

GENERAL PROCEDURE FOR THE PREPARATION OF ARYL-TERMINAL ACIDS

Example 12

9-Phenoxynonanoic Acid

A. 7-Phenoxyheptyl bromide, Phenol (3.10 g, 33 mmol), 1,7-dibromoheptane (7.74 g, 30 mmol) and NaOH (1.34 g, 33 mmol) were refluxed in EtOH (40 mL) for 30 h. After cooling to room temperature, water (150 mL) was added and the mixture was extracted with ethyl acetate (4×50 mL). The organic phase was washed with water (50 mL) and brine (50 mL), and the mixture was dried over Na$_2$SO$_4$. After evaporation of solvent, the residue was purified by Kugelrohr distillation to give 7-phenoxyheptyl bromide (2.46 g, 30%), bp 126–130° C./0.10 torr, $^1$H-NMR: 1.2–1.9 (m, 10H), 3.36 (t, 2H), 3.91 (t, 2H), 6.7–7.2 (m, 5H).

B. Ethyl 2-ethoxycarbonyl-9-phenoxynonanoate. Sodium (0.22 g, 9.6 mmol) was dissolved in EtOH (20 mL). Diethyl malonate (1.53 g, 9.6 mmol) in EtOH (5 mL) and 7-phenoxyheptyl bromide (2.36 g, 8.7 mmol) in EtOH (5 mL) were subsequently added at room temperature. The reaction mixture was refluxed for 8 h. After evaporation of the solvent, the residue was taken up in ethyl acetate (150 mL). The organic phase was washed with water (2×50 mL), and brine (50 mL), and dried over $Na_2SO_4$. The crude product was purified by Kugelrohr distillation to give ethyl 2-ethoxycarbonyl-9-phenoxynonanoate (1.92 g, 63%), bp 150–154° C./0.1 torr, $^1$H-NMR: 1.24 (t, 6H), 1.1–1.8 (in, 12H), 3.30 (t, 1H), 3.91 (t, 2H), 4.18 (q, 4H), 6.7–7.2 (m, 5H).

C. 9-Phenoxynonanoic acid. A solution of ethyl 2-ethoxycarbonyl-9-phenoxynonanoate (1.84 g, 5.3 mmol) in 20% NaOH (20 mL) was refluxed for 10 h. The solution was acidified with HCl (pH=2) and extracted with ethyl acetate (3×50 mL). The organic phase was-washed with water (2×30 mL), and brine (30 mL), and dried over $Na_2SO_4$. After removal of the solvent in vacuo, the residue was heated on an oil bath at 180–200° C. for 10 min. The crude product was distilled (Kugelrohr) followed by crystallization (hexane) to give the product (1.14 g, 85%), mp 66.5–67.5° C. (lit.[3] 68–69° C.). IR: 3450-2550, 1720 $cm^{-1}$; $^1$H-NMR: 1.26–1.39 (m, 8H), 1.61 (q, 2H), 1.75 (q, 2H), 2.34 (t, 2H), 3.93 (t, 2H), 6.83–6.96 (m, 3H), 7.28 (t, 2H), 10.8 (bs, 1H).

Example 13

9-Phenylthionanoic acid

A. 7-Phenylthioheptyl bromide was prepared from thiophenol (4.40 g, 40 mmol) and 1,7-dibromoheptane (10.32 g, 40 mmol) as described above for 7-phenoxyheptyl bromide. Yield: 46% bp; 132–136° C./0.05 torr; 1H-NMR: 1.30–1.85 (m, 10H), 2.90 (t, 2H), 3.35 (t, 2H), 7.25 (s, 5H)).

B. Ethyl 2-ethoxycarbonyl-9-phenylthiononanoate was prepared from 7-phenylthioheptyl bromide (4.31 g, 15 mmol) and diethyl malonate (3.20 g, 20 mmol) according to the procedure given above. Yield: 68%, bp: 174–178° C./0.05 torr; $^1$H-NMR: 1.15–1.90 (m, 18H), 2.90 (t, 2H), 3.30 (t, 1H), 4.20 (q, 4H), 7.25 (s, 5H).

C. 9-Phenylthiononanoic acid was obtained from ethyl 2-ethoxycarbonyl-9-phenylthiononanoate (3.66 g, 10 mmol) by basic hydrolysis as described above. Yield: 82%, mp 67–68° C.; IR: 3450-2550, 1695 $cm^{-1}$; $^1$H-NMR: 1.20–1.80 (m, 12H), 2.35 (t, 2H), 2.85 (t, 2H), 7.20 (s, 5H), 10.50 (bs, 1H). Anal. Calcd. for $C_{15}H_{22}O_2S$: C, 67.63; H, 8.32; S, 12.03%. Found: C, 67.54; H, 8.31; S, 12.09%.

Example 14

8-Benzyloxyoctanoic Acid

A. 6-Benzyloxyhexyl bromide was prepared from benzyl alcohol (4.75 g, 44 mmol) and 1,6-dibromohexane (9.76 g, 40 mmol) using the general procedure given above. Yield: 36%, bp 100–105° C./torr: $^1$H-NMR: 1.2–1.9 (m, 8H), 3.37 (t, 4H), 4.46 (s, 2H), 7.28 (m, 5H).

B. Ethyl 2-ethoxycarbonyl-8-benzyloxyoctanoate was prepared from 6-benzyloxyhexyl bromide (3.52 g, 13 mmol) and diethyl malonate (2.29 g, 14 mmol) according to the general procedure given above. Yield 60%, bp 152–158° C./0.15 torr. $^1$H-NMR: 1.24 (t, 6H), 1.2–1.9 (m, 10H), 3.43 (t, 2H), 4.18 (q, 4H), 4.45 (s, 2H), 7.27 (m, 5H).

C. 8-Benzyloxyoctanoic acid was prepared from ethyl 2-ethoxycarbonyl-8-benzyloxyoctanoate (2.6 g, 7.4 mmol) by basic hydrolysis as described above. Yield: 83%, bp 158–162° C./0.15 torr; IR: 3450-2550, 1710 $cm^{-1}$; $^1$H-NMR: 1.24–1.43 (m, 6H), 1.54–1.69 (m, 4H), 2.31 (t, 2H), 3.46 (t, 2H), 4.51 (s, 2H), 7.23–7.38 (m, 5H), 9.55 (bs, 1H). Anal. Calcd. for $C_{15}H_{22}O_3$: C, 71.97; H, 8.86%. Found: C, 71.83; H, 8.90%.

Example 15

8-Benzylthiooctanoic Acid

A. Ethyl 8-benzylthiooctanoate. NaH (0.63 g, 16 mmol) was washed with hexane and then suspended in dry THF (60 mL). Benzylmercaptan (1.86 g, 15 mmol) in THF (20 mL) was added and the mixture stirred for 30 min at room temperature. Ethyl 8-iodooctanoate (4.47 g, 15 mmol) in THF (20 mL) was added and the mixture was refluxed for 12 h. After evaporation of the solvent, the residue was dissolved in ethyl acetate (150 mL). The organic phase was washed with water (2×50 mL), and brine (50 mL) and dried over $Na_2SO_4$. The crude product was purified by column chromatography on silica gel with ethyl acetate:hexane (1:5) and subsequent Kugelrohr distillation to give ethyl 8-benzylthiooctanoate (3.7 g, 84%), bp 134–138° C./0.15 torr. $^1$H-NMR: 1.21 (t, 3H), 1.2–1.8 (m, 10H), 2.27 (t, 4H), 3.68 (s, 2H), 4.09 (q, 2H), 7.24 (m, 5H).

B. 8-Benzylthiooctanoic acid. A solution of ethyl 8-benzylthiooctanoate (2.94 g, 10 mmol) and 1M NaOH (60 mL, 60 mmol) in MeOH (30 mL) was heated at 70° C. for 6 h. The reaction mixture was acidified with HCl (pH=1) and extracted with ethyl acetate (150 mL). The organic phase was washed with water (2×50 mL), and brine (50 mL), and dried over $Na_2SO_4$. The crude product was purified by crystallization from hexane to afford the product (2.45 g, 92%), mp 37–37.5° C.; IR: 3400-2500, 1700 $cm^{-1}$; $^1$H-NMR: 1.18–1.43 (m, 6H), 1.52 (q, 2H), 1.61 (q, 2H), 2.33 (t, 2H), 2.39 (t, 2H), 3.69 (s, 2H), 7.12–7.38 (m, 5H), 9.45 (bs, 1H). Anal. Calcd. for $C_{15}H_{22}SO_2$: C, 67.63, H, 8.32%; Found: C, 67.74, H, 8.35%.

Example 16

8-(p-Propylphenyl)-7-octenenitrile.

This compound was synthesized from 6-cyanohexyltriphenylphosphonium bromide (9.05 g, 20 mmol) and p-propylbenzaldehyde (2.96 g, 20 mmol) in THF (100 mL) by a Wittig reaction. Kugelrohr distillation afforded the product (3.25 g, 67%) as a colorless liquid (bp 144–148° C./0.05 torr). IR 2290 $cm^{-1}$; $^1$H-NMR: 0.95 (t, 3H), 1.55 (m, 8H), 2.40 (m, 6H), 5.60 (in, 1H), 6.40 (d, 1H), 7.10 (s, 4H).

Example 17

8-(p-Propylphenyl)-7-octenoic acid.

This compound was synthesized from 8-(p-propylphenyl)-7-octenenitrile (2.41 g, 10 mmol) by a hydrolysis reaction. Kugelrohr distillation afforded the product (2.36 g, 90%) as a colorless oil (bp 148–152° C./0.05 torr). IR: 3400-2500, 1720 $cm^{-1}$; $^1$H-NMR: 0.95 (t, 3H), 1.45 (m, 8H), 2.45 (m, 6H), 5.65 (m, 1H), 6.40 (d, 1H), 7.15 (s, 4H), 11.30 (bs, 1H). Anal. Calcd. for $C_{17}H_{24}O_2$: C, 78.42, H, 9.29%; Found: C, 78.43, H, 9.30%. Z:E=88:12.

Example 18

8-(p-Propylphenyl)octanoic acid.

This compound was synthesized from 8-(p-propylphenyl)-7-octenoic acid (1.30 g, 5 mmol) and $Pd/BaSO_4$ (130 mg) by a hydrogenation reaction. Crystallization (petroleum ether) afforded the product (1.25 g, 95%) as white crystals (mp 42–43° C.). IR: 3400-2500, 1705 $cm^{-1}$; $^1$H-NMR: 0.95 (t, 3H), 1.45 (m, 12H), 2.50 (m, 6H), 7.05 (s, 4H), 11.40 (bs, 1H). Anal. Calcd. for $C_{17}H_{26}O_2$: C, 77.82, H, 9.99%; Found: C, 77.75, H, 10.04%.

Example 19

7-(p-Butylphenyl)-6-heptenoic acid.

This compound was synthesized from 5-carboxypentyltriphenylphosphonium bromide (9.50 g, 20 mmol) and p-butylbenzaldehyde (3.24 g, 20 mmol) in THF (100 mL) by a Wittig reaction. Kugelrohr distillation yielded the product (2.67 g, 51%) as a colorless oil (bp 154–157° C./0.05 torr). IR: 3400-2500, 1720 cm$^{-1}$, $^1$H-NMR:0.92 (t, 3H), 1.50 (m, 8H), 2.30 (m, 4H), 2.58 (m, 2H), 5.58+6.15 (m, 1H), 6.38 (t, 1H), 7.18 (m, 4H), 10.30 (bs, 1H). Anal. Calcd. for $C_{17}H_{24}O_2$: C, 78.42, H, 9.29%; Found: C, 78.38, H. 9.29%. Z:E=62:38.

Example 20

7-(p-Butylphenyl heptanoic acid.

This compound was synthesized from 7-(p-butylphenyl)-6-heptenoic acid (1.30 g, 5 mmol) by a hydrogenation reaction using Pd/C (130 mg). Crystallization (petroleum ether) afforded the product (1.19 g, 97%) as white crystals (mp 32–33° C.). IR: 3400-2500, 1718 cm$^{-1}$; $^1$H-NMR:0.92 (t, 3H), 1.35 (m, 6H), 1.60 (m, 6H), 2.32 (t, 2H), 2.55 (m, 4H), 7.02 (s, 4H), 9.70 (bs, 1H). Anal. Calcd. for $C_{17}H_{26}O_2$: C, 77.82, H, 9.99%; Found: C, 77.73, H, 10.01%.

Example 21

6-(R-Pentylphenyl)-5-hexenoic acid.

This compound was synthesized from p-pentylbenzaldehyde (3.52 g, 20 mmol, prepared from p-pentylbenzoyl chloride and lithium tri(t-butoxy)aluminum hydride) and 4-carboxybutyltriphenylphosphonium bromide (8.86 g, 2, mmol) in THF (100 mL) by a Wittig reaction. Kugelrohr distillation (bp 147–151° C./0.05 torr) afforded the product (2.49 g, 48%). IR: 3400-2500, 1725 cm$^{-1}$; $^1$H-NMR: 0.90 (t, 3H), 1.28 (m, 6H), 1.82 (m, 2H), 1.37 (m, 4H), 2.57 (t, 2H), 5.55+6.10 (m, 1H), 6.38 (m, 1H), 7.10 (m, 4H), 10.50 (bs, 1H). Anal. Calcd. for $C_{17}H_{24}O_2$: C, 78.42, H, 9.29%; Found: C, 78.22, H, 9.27%. Z:E=35:65.

Example 22

6-(p-Pentylphenyl)hexanoic acid.

This compound was synthesized from 6-(p-pentylphenyl)-5-hexenoic acid (1.30 g, 5 mmol) by hydrogenation reaction using Pd/C (130 mg). Crystallization (petroleum ether) afforded the product (1.13 g, 87%) as white crystals (mp 29–30° C.), IR: 3400-2500, 1730 cm$^{-1}$; $^1$H-NMR: 0.89 (t, 3H), 1.32 (m, 6H), 1.60 (m, 6H), 2.35 (t, 2H), 2.58 (m, 4H), 7.07 (s, 1H), 10.30 (bs, 1H). Anal. Calcd. for $C_{17}H_{26}O_2$: C, 77.82, H, 9.99%; Found: C, 77.56, H, 9.90%.

Example 23

7-(p-Propoxyphenyl)-6-heptenoic acid.

This compound was synthesized from p-propoxybenzaldehyde (3.26 g, 20 mmol, prepared from 1-bromopropane and 4-hydroxybenzaldehyde) and 5-carboxypentyltriphenylphosphonium bromide (9.50 g, 20 mmol) in THF (100 mL) by a Wittig reaction. Crystallization (petroleum ether) afforded the product (3.15 g, 60%) as white crystals (mp: 52–53° C.). IR: 3450-2500, 1730 cm$^{-1}$; $^1$H-NMR: 1.00 (t, 3H), 1.48 (m, 2H), 1.67 (m, 2H), 1.82 (m, 2H), 2.35 (m, 4H), 3.92 (t, 2H), 5.72+6.05 (m, 1H), 6.35 (d, 1H), 7.05 (q, 4H), 10.40 (bs, 1H). Anal. Calcd. for $C_{16}H_{22}O_3$: C, 73.25, H, 8.45%. Found: C, 73.15, H, 8.45%. Z:E=30:70.

Example 24

7(p-Propoxyphenyl)heptanoic acid.

This compound was synthesized from 7-(p-propoxyphenyl)-6-heptenoic acid (1.31 g, 5 mmol) by hydrogenation reaction using Pd/C (130 mg). Crystallization (petroleum ether) afforded the product (1.23 g, 93%) as white crystals (mp: 49–50° C.). IR: 3450-2550, 1725 cm$^{-1}$; $^1$H-NMR: 1.00 (t, 3H), 1.37 (m, 4H), 1.60 (m, 4H), 1.79 (m, 2H), 2.36 (t, 2H), 2.53 (t, 2H), 3.87 (t, 2H), 6.95 (q, 4H), 9.80 (bs, 1H). Anal. Calcd. for $C_{16}H_{24}O_3$: C, 72.69, H, 9.15%; Found: C, 72.79, H, 9.16%.

Example 25

6-(R-Butoxyphenyl)-5-hexenoic acid.

This compound was synthesized from 4-carboxybutyltriphenylphosphonium bromide (8.86 g, 20 mmol) and p-butoxybenzaldehyde (3.56 g, 20 mmol) in THF (100 mL) by a Wittig reaction. Crystallization (petroleum ether) afforded the product (3.82 g, 73%) as white crystals (mp: 56–57° C.). IR: 3350-2500, 1700 cm$^{-1}$ $^1$H-NMR: 1.00 (t, 3H), 1.50 (m, 2H), 1.80 (m, 4H), 2.40 (m, 4H), 3.90 (t, 2H), 5.50+6.00 (m, 1H), 6.38 (q, 1H), 7.05 (q, 4H), 11.00 (bs, 1H). Anal. Calcd. for $C_{16}H_{22}O_3$: C, 73.25, H, 8.45%; Found: C, 73.32, H, 8.46%. Z:E=37:63.

Example 26

6-(p-Butoxyphenyl)hexanoic acid.

This compound was synthesized from 6-(p-butoxyphenyl)-5-hexenoic acid (2.62 g, 10 mmol) by a hydrogenation reaction using Pd/C (260 mg). Crystallization (petroleum ether) afforded the product (2.49 g, 94%) as white crystals (mp 39–40° C.). IR: 3400-2500, 1705 cm$^{-1}$; $^1$H-NMR: 0.96 (t, 3H), 1.35 (m, 2H), 1.50 (m, 2H), 1.62 (m, 4H), 1.75 (m, 2H), 2.35 (t, 2H), 2.52 (t, 2H), 3.92 (t, 2H), 6.95 (q, 4H), 10.30 (bs, 1H). Anal. Calcd. for $C_{16}H_{24}O_3$: C, 72.69, H, 9.15%; Found: C, 72.78, H, 9.18%.

Example 27

Ethyl 8-(4-ethyl)phenoxyoctanoate. NaH (0.25 g, 11 mmol) was washed with hexane and then suspended in dry THF (50 mL). 4-Ethylphenol (1.22 g, 10 mmol) in THF (20 mL) was added and stirred for 30 min at room temperature. Ethyl 8-iodooctanoate (2.98 g, 10 mmol) in THF (20 mL) was added and the mixture was refluxed for 12 h. After evaporation of the solvent, the residue was dissolved in ethyl acetate (150 mL), and the organic phase was washed with water (2×50 mL), and brine (50 mL) and dried over $Na_2SO_4$. The crude product was purified by column chromatography on silica gel (ethyl acetate:hexane=1:5) and subsequent Kugelrohr distillation to give the product (0.85 g, 24%), bp 122–126° C./0.1 torr. IR: 1740 cm$^{-1}$; $^1$H-NMR: 1.19 (t, 3H), 1.25 (t, 3H), 1.30–1.80 (m, 10H), 2.28 (t, 2H), 2.57 (q, 2H), 3.90 (t, 2H), 4.12 (q, 2H), 6.86 (d, 2H), 7.08 (d, 2H).

Example 28

8-(4-Ethyl)phenoxyoctanoic acid.

This compound was synthesized from ethyl 8-(4-ethyl)phenoxyoctanoate (1.76 g, 5 mmol) by a hydrolysis reaction. Crystallization from hexane gave white crystals (1.40 g, 87%), mp 77–78° C.; IR: 3450-2950, 1720 cm$^{-1}$; $^1$H-NMR: 1.17 (t, 3H), 1.29–1.49 (m, 6H), 1.63 (q, 2H), 1.74 (q, 2H), 2.31 (t, 2H), 2.56 (q, 2H), 3.88 (t, 2H), 6.77 (d, 2H), 7.06 (d, 2H), 10.2 (bs, 1H). Anal. Calcd. for $C_{16}H_{24}O_3$: C, 72.69, H. 9.15%; Found: C, 72.53, H, 9.19%.

Example 29

12-Phenyl-11-dodecenoic acid.

This compound was synthesized from 10-carboxydecyltriphenylphosphonium bromide (10.55 g, 20 mmol) and benzaldehyde (2.12 g, 20 mmol) in THF (100 mL) by a Wittig reaction. Kugelrohr distillation (bp 152–155° C./0.03 torr) and crystallization afforded the product (2.43 g, 44%) as white crystals (mp 27–27.5° C.). IR: 3400-2500, 1720, 700 cm$^{-1}$; $^1$H-NMR: 1.30 (m, 10H), 1.40 (m, 2H), 1.62 (m, 2H), 2.35 (m, 4H), 5.65 (m, 1H), 6.40 (m, 1H), 7.25 (m, 5H), 10.40 (bs, 1H). Anal. Calcd. for $C_{18}H_{26}O_2$: C, 78.79, H, 9.55%; Found: C, 78.66, H, 9.60%. Z:E=93:7.

Example 30

12-Phenyldodecanoic acid.

This compound was synthesized from 12-phenyl-10-dodecenoic acid (1.92 g, 7 mmol) by a hydrogenation reaction using Pd/C (190 mg). Crystallization (petroleum ether) afforded the product (1.88 g, 97%) as white crystals (mp 47–48° C.). IR: 3400-2500, 1700 cm$^{-1}$; $^1$H-NMR: 1.30 (m, 14H), 1.60 (m, 4H), 2.32 (t, 2H), 2.57 (t, 2H), 7.20 (m, 5H), 10.20 (bs, 1H). Anal. Calcd. for $C_{18}H_{28}O_2$: C, 78.21, H, 10.21%;

Found: C, 78.29, H, 10.25%.

HETEROAROMATIC ANALOGS

Example 31

9-(2-Furyl)-8-nonenoic acid.

This compound was synthesized from 7-carboxyheptyltriphenylphosphonium bromide (9.71 g, 20 mmol) and 2-furaldehyde (1.92 g, 20 mmol) in THF (100 mL) by a Wittig reaction. Kugelrohr distillation yielded the product (2.69 g, 61%) as a pale yellow oil (bp 136–139° C./0.05 torr). IR: 3500-2500, 1730, 710 cm$^{-1}$; $^1$H-NMR: 1.40 (m, 8H), 2.35 (m, 4H), 5.55 (m, 1H), 6.30 (m, 3H), 7.35 (s, 1H), 11.40 (bs, 1H). Anal. Calcd. for $C_{13}H_{18}O_3$: C, 70.25, H, 8.16%; Found: C, 69.98, H, 8.26%. Z:E=79:21.

Example 32

9-(2-Furyl)nonanoic acid.

This compound was synthesized from 9-(2-furyl)-8-nonenoic acid (0.89 g, 4 mmol) by a hydrogenation reaction using Pd/BaSO$_4$ (90 Mg). Crystallization (petroleum ether) afforded the product (0.84 g, 93%) as white crystals (mp 31–32° C.); IR: 3450-2500, 1720 cm$^{-1}$; $^1$H-NMR: 1.30 (m, 8H), 1.63 (m, 4H), 2.35 (t, 2H), 2.60 (t, 2H), 5.95 (s, 1H), 6.27 (s, 1H), 7.28 (s, 1H), 9.85 (bs, 1H). Anal. Calcd. for $C_{13}H_{20}O_3$: C, 69.61, H. 8.99%; Found: C, 69.42, H. 9.04%.

Example 33

9-(2-(5-Methyl)furyl)-8-nonenoic acid.

This compound was synthesized from 5-methylfurfural (2.20 g, 20 mmol) and 7-carboxyheptyltriphenylphosphonium bromide (9.71 g, 20 mmol) in THF (100 mL) by a Wittig reaction. Kugelrohr distillation afforded the product (2.35 g, 50%) as a yellow oil (bp 140–143° C./0.05 torr).

IR: 3400-2500, 1720 cm$^{-1}$; $^1$H-NMR: 1.36 (m, 4H), 1.45 (m, 2H), 1.65 (m, 2H), 2.28 (s, 3H), 2.37 (t, 2H), 2.41 (m, 2H), 5.45 (m, 1H), 5.95 (d, 1H), 6.12 (s, 1H), 10.00 (bs, 1H). Anal. Calcd. for $C_{14}H_{20}O_3$: C, 71.16, H, 8.53%; Found: C, 70.85, H, 8.63%. Z:E=9:91.

Example 34

9-(2-(5-Methyl)furyl)nonanoic acid.

This compound was synthesized from 9-(2-(5-methyl)furyl)-8-nonenoic acid (0.94 g, 4 mmol) by a hydrogenation reaction using Pd/BaSO$_4$ (94 mg). Crystallization (petroleum ether) afforded the product (0.87 g, 92%) as white crystals (mp 49–50° C.) ; IR: 3400-2500, 1710 cm$^{-1}$; $^1$H-NMR: 1.30 (m, 8H), 1.60 (m, 4H), 2.23 (s, 3H), 2.32 (t, 2H), 2.55 (t, 2H), 5.81 (s, 2H), 8.95 (bs, 1H). Anal. Calcd. for $C_{14}H_{22}O_3$: C, 70.56, H, 9.30%; Found: C, 70.39, H, 9.33%.

Example 35

11-(2-furyl)-10-undecenoic acid.

This compound was synthesized from 2-furaldehyde (1.92 g, 20 mmol) and 9-carboxynonyltriphenylphosphonium bromide (10.27 g, 20 mmol) in THF (100 mL) by a Wittig reaction. Crystallization (petroleum ether) afforded the product (2.95 g, 59%) as white crystals (mp 45–46° C.); IR: 3450 -2500 cm$^{-1}$; $^1$H-NMR: 1.33 (m, 8H), 1.46 (m, 2H), 1.65 (m, 2H), 2.34 (t, 2H), 2.45 (m, 2H), 5.55 (m, 1H), 6.18 (d, 1H), 6.25 (d, 1H), 6.38 (d, 1H), 7.38 (s, 1H), 9.80 (bs, 1H). Anal. Calcd. for $C_{15}H_{22}O_3$:C, 71.97, H, 8.86%; Found: C, 71.93, H, 8.87%. Z:E=43:57.

Example 36

11-(2-Furyl)undecanoic acid.

This compound was synthesized from 11-(2-furyl)-10-undecenoic acid (1.25 g, 5 mmol) by a hydrogenation reaction using Pd/BaSO$_4$ (125 mg). Crystallization (petroleum ether) afforded the product (1.13 g, 90%) as white crystals (mp 40–41° C.); IR: 3450-2500, 1720 cm$^{-1}$; $^1$H-NMR: 1.30 (m, 12H), 1.65 (m, 4H), 2.34 (t, 2H), 2.60 (t, 2H), 5.95 (d, 1H), 6.28 (d, 1H), 7.30 (s, 1H), 10.10 (bs, 1H). Anal. Calcd. for $C_{15}H_{24}O_3$: C, 71.39, H, 9.58%; Found: C, 71.21, H, 9.63%.

Example 37

12-(2-Furyl)-11-dodecenoic acid.

This compound was synthesized from 10-carboxydecyltriphenylphosphonium bromide (10.50 g, 20 mmol) and furfural (1.92 g, 20 mmol) in THF (100 mL) by a Wittig reaction. Crystallization afforded the product (2.38 g, 45%) as pale yellow crystals (mp 38–39° C.); IR: 3450-2500, 1715, 695 cm$^{-1}$; $^1$H-NMR: 1.35 (m, 14H), 2.35 (t, 4H), 5.60 (m, 1H), 6.30 (m, 3H), 7.35 (s, 1H), 9.40 (bs, 1H). Anal. Calcd. for $C_{16}H_{24}O_3$: C, 72.69, H, 9.15; Found: C, 72.44, H, 9.06%. Z:E=43:57.

Example 38

9-(2-Thienyl)-8-nonenoic acid.

This compound was synthesized from 7-carboxyheptyl-triphenylphosphonium bromide (9.71 g, 20 mmol) and 2-thiophenecarboxaldehyde (2.24 g, 20 mmol) in THF (100 mL) by a Wittig reaction. Crystallization afforded the product (2.79 g, 59%) as white crystals (mp 45–46° C.). IR: 3400-2500, 1720, 710 cm$^{-1}$; $^1$H-NMR: 1.45 (m, 8H), 2.35 (m, 4H), 5.55 (m, 1H), 6.50 (d, 1H), 7.00 (m, 3H), 11.00 (bs, 1H). Anal. Calcd. for $C_{13}H_{18}SO_2$: C, 65.51, H, 7.61%; Found: C, 65.58, H, 7.63%. Z:E=75:25.

Example 39

9-(2-Thienyl)-nonanoic acid.

This compound was synthesized from 9-(2-thienyl)-8-nonenoic acid (1.19 g, 5 mmol) by a hydrogenation reaction using Pd/C. (120 mg). Crystallization afforded the product (1.05 g, 88%) as white crystals (mp 32–33° C.); IR: 3400-2500, 1715, 705 cm$^{-1}$; $^1$H-NMR: 1.35 (m, 12H), 2.35 (t, 2H), 2.85 (t, 2H), 6.95 (m, 3H), 10.35 (bs, 1H). Anal. Calcd. for $C_{13}H_{20}SO_2$: C, 64.96, H, 8.39%; Found: C, 64.81, H, 8.43%.

Example 40

9-(2-(5-Methyl) thienyl)-8-nonenoic acid.

This compound was synthesized from 7-carboxyheptyl-phenylphosphonium bromide (7.28 g, 15 mmol) and 2-(5-methyl)thiophenecarboxaldehyde (1.92 g, 15 mmol) in THF (100 mL) by a Wittig reaction. Kugelrohr distillation (bp 155–159° C./0.05 torr) and crystallization (petroleum ether) afforded the product (2.43 g, 48%) as pale yellow crystals (mp 38–39° C.). IR: 3400-2500, 1715 cm$^{-1}$; $^1$H-NMR: 1.40 (m, 6H), 1.65 (m, 2H), 2.37 (m, 4H), 2.45 (s, 3H), 5.45+5.90 (m, 1H), 6.41 (t, 1H), 6.65 (m, 1H), 6.75 (d, 1H), 10.05 (bs, 1H). Anal. Calcd. for $C_{14}H_{20}O_2S$: C, 66.63, H, 7.99%; Found: C, 66.54, H, 8.02%. Z:E=72:28.

Example 41

9-(2-(5-Methyl)thienyl)nonanoic acid.

This compound was synthesized from 9-(2-(5-methyl)thienyl)- 8-nonenoic acid (1.01 g, 4 mmol) by a hydrogenation reaction using Pd/C (200 mg). Crystallization (petroleum ether) afforded the product (0.91 g, 89%) as white crystals (mp 39–40° C.). IR: 3400-2500, 1720 cm$^{-1}$; $^1$H-NMR: 1.32 (m, 8H), 1.63 (m, 4H), 2.32 (t, 2H), 2.45 (s, 3H), 2.71 (t, 2H), 6.54 (s, 2H), 9.50 (bs, 1H). Anal. Calcd. for $C_{14}H_{22}O_2S$: C, 66.10, H, 8.72%; Found: C, 65.97, H, 8.72%.

Example 42

11-(2-Thienyl)-10-undecenoic acid.

This compound was synthesized from 2-thiophenecarboxaldehyde (2.24 g, 20 mmol) and 9-carboxynonyltriphenylphosphonium bromide (10.27 g, 20 mmol) in THF (100 mL) by a Wittig reaction. Crystallization (hexanes-ethyl acetate) afforded the product (2.45 g, 46%) as white crystals (mp 61–62° C.); IR: 3450-2500, 1715 cm$^{-1}$; $^1$H-NMR: 1.31 (m, 8H), 1.45 (m, 2H), 1.65 (m, 2H), 2.34 (t, 2H), 2.38 (t, 2H), 5.55 (m, 1H), 6.50 (d, 1H), 6.95 (m, 2H), 7.23 (d, 2H), 10.05 (bs, 1H). Anal. Calcd. for $C_{15}H_{22}O_2S$: C, 67.63, H, 8.32%; Found: C, 67.60, H, 8.34%. Z:E=19:81.

Example 43

11-(2-Thienyl)undecanoic acid.

This compound was synthesized from 11-(2-thienyl)-10-undecenoic acid (800 mg, 3 mmol) by a hydrogenation reaction using Pd/C (80 mg). Crystallization (petroleum ether) afforded the product (0.73 g, 91%) as white crystals (mp 41–42° C.): IR: 3450-2500, 1715 cm$^{-1}$; $^1$H-NMR: 1.30 (m, 12H), 1.63 (m, 4H), 2.32 (t, 2H), 2.80 (t, 2H), 6.78 (d, 1H), 6.90 (t, 1H), 7.10 (d, 1H), 9.80 (bs, 1H). Anal. Calcd. for $C_{15}H_{24}O_2S$: C, 67.12, H, 9.01%; Found: C, 67.55, H, 8.89%.

Example 44

The biological activity of a panel of fatty acid analogs that had been tested previously as substrates for purified *E. coli*-derived *S. cerevisiae* myristoylCoA:protein N-myristoyltransferase (Nmt) were tested for toxicity against trypanosomes as potential candidates for anti-trypanosomal drugs. For purposes of comparison, several oxatetradecanoic acids described in U.S. Pat. No. 5,151,445 as inhibitors of the growth and viability of bloodstream trypanosome parasites were included in the test panel. For convenience, this panel of fatty acid analogs was subdivided based on chemical differences in their secondary functional group. These functional groups vary with respect to their polarity, steric bulk, conformations, and to a limited degree, overall chain length. The 247 compounds thus tested are organized in Table 2, below, into 20 families. Several of these functional groups should have complex effects on both conformation and stereoelectronic properties (e.g. analogs with ester) whereas others will predominantly affect only one of these properties (e.g. conformation but not polarity in the case of olefins; polarity but not conformation in the case of oxatetradecanoic acids). In many of these families, the effects of the functional group have been assessed at every possible position from C3 through C13 in tetradecanoic acid (e.g. see the thia-and oxotetradecanoic acids listed in Table 2).

Figure 1:
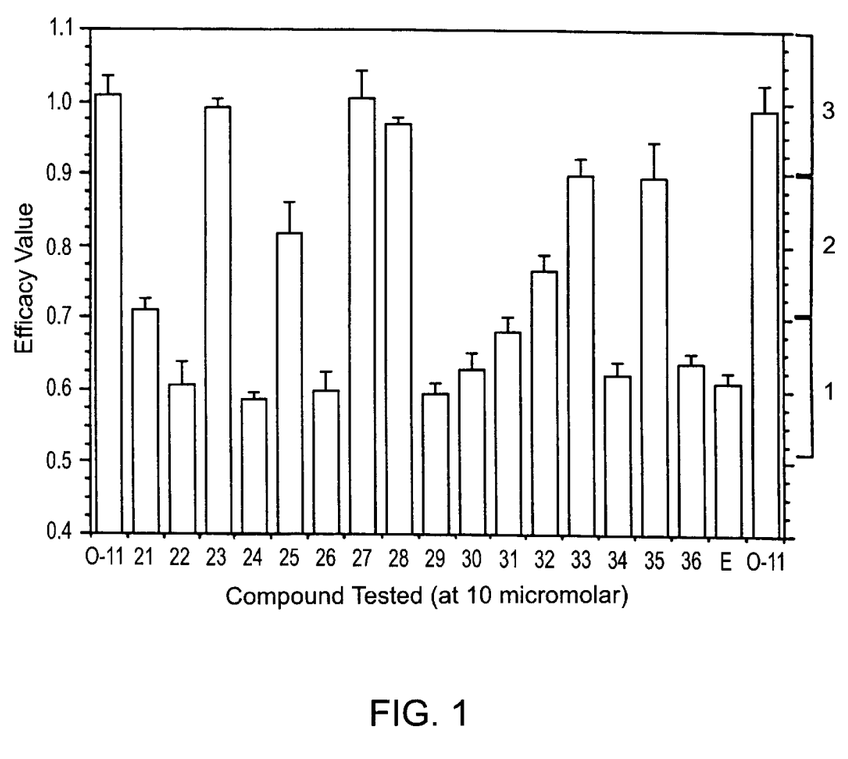

To perform the large scale testing, a reproducible and rapid assay was employed. The method exploits the fact that growing trypanosomes secrete large amounts of pyruvic acid, an end product of glucose catabolism (Operdoes, 1987). The pyruvic acid causes a change in color of the phenol red indicator present in the culture medium, providing a quantitative measure of cell growth. A similar assay has been published previously (Zinsstag et al., 1991). The detailed assay procedures used herein are as follows:

Trypanosomes were grown in the presence of analogs or positive and negative controls (11-oxatetradecanoic acid and the ethanol solvent, respectively). To avoid bias in data interpretation analog solutions were identified only by a code number. To evaluate reliability and reproducibility of the assay, several analogs were coded twice. All coded analogs were tested in quadruplicate on at least two separate occasions. After a standard growth period, the absorbance of the culture was determined at 550 nm and 405 nm and an efficacy value calculated from the ratio of these absorbances. Results from a representative test are shown in FIG. 1. This set of coded compounds included samples of ethanol and 11-oxatetradecanoic acid as both coded and uncoded samples (compounds E and 24 and O11 and 27 respectively). The excellent agreement between these samples and the controls attests to the reproducibility of this assay. Quadruplicate samples were generally each within 5% of the mean, and the ratio of the absorbance at 550 nm and 405 nm obtained for 11-oxatetradecanoic acid averaged 1.12 with a standard error of 0.04 for over 100 determinations during a 6 month period.

The analogs were grouped in terms of efficacy, defining 10 $\mu$M 11-oxatetradecanoic acid as the center of group 3 and the ethanol controls as the center of group 1 (FIG. 1). The range of values were calculated defining each group independently for each test based on the 11-oxatetradecanoic acid and ethanol values in that trial. This controlled for any differences in medium or cell growth. All compounds classified as group 3 were tested at-least twice. After screening and categorizing all analogs in this manner, the code was broken and the structures of the compounds were matched with their efficacy. Note that 11-oxa-, 13-oxa-, and 6-oxatetradecanoic acids fall in groups 3, 2, and 1, respectively. These values correlate well with their effects on trypanosome growth assessed by cell counts using a hemocytometer (Doering et al., 1991).

Figure 2A:
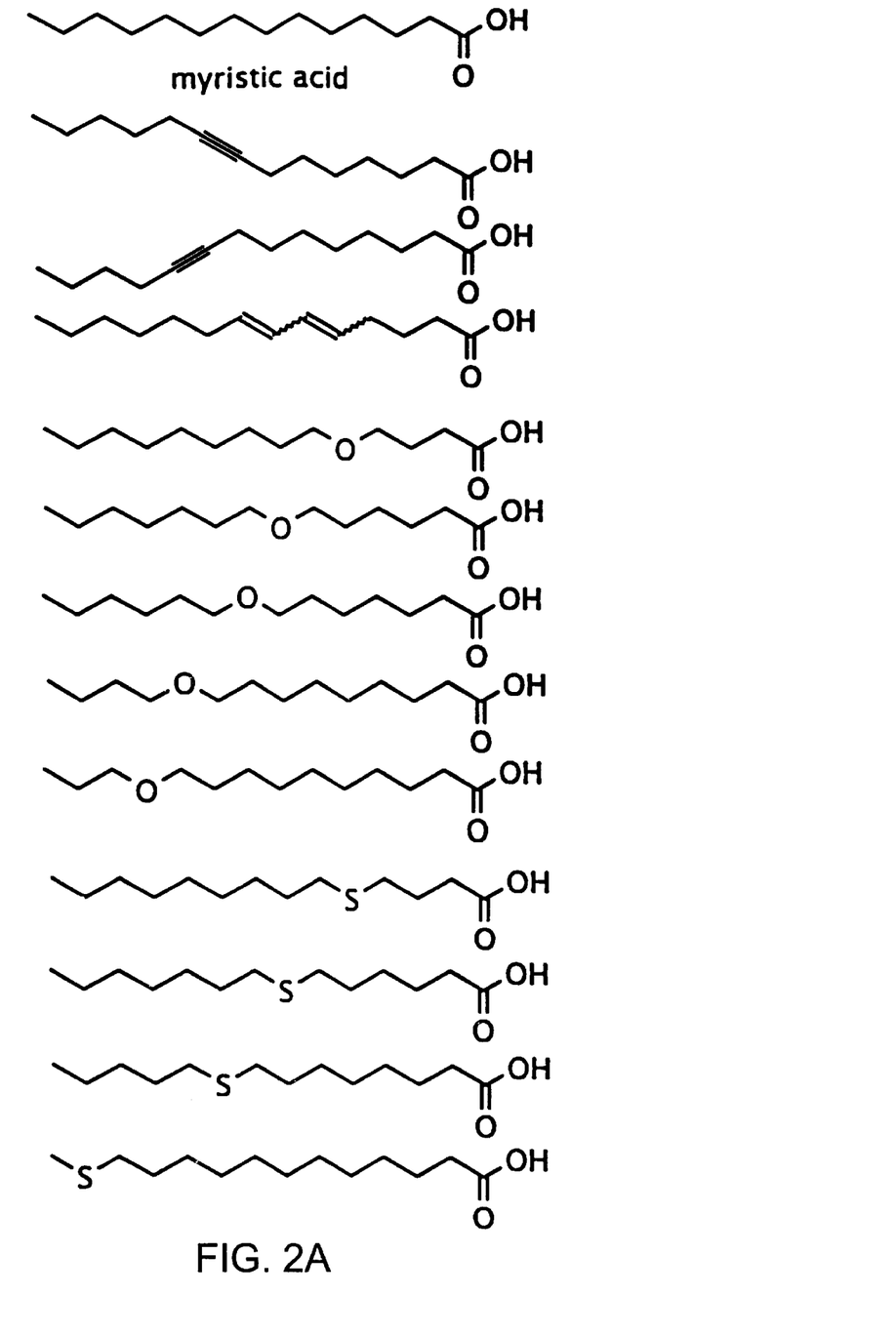
FIGS. 2A and 2B show the chemical structures of the 20 myristate analogs most toxic to trypanosomes arranged into structural groups.
Figure 2B:
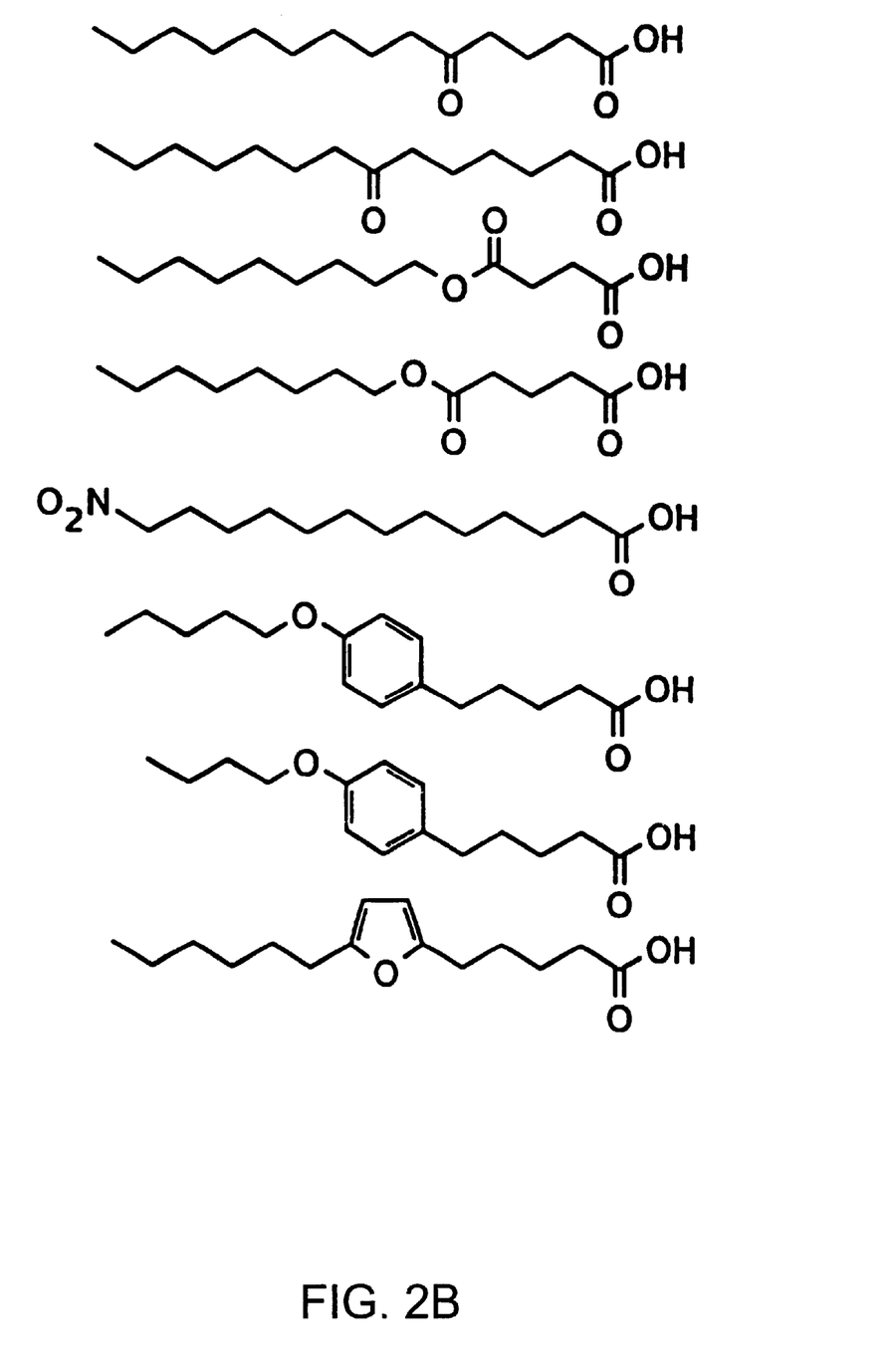

FIG. 2 shows the structures of the 20 most active compounds which collectively define group 3. They are presented in decreasing order of potency in Table 1, above, and as structural groups in FIG. 2. Nine of the compounds are either thiatetradecanoic or oxatetradecanoic acids. The ether functional group is also present in conjunction with an aromatic residue in three other compounds. An additional four analogs contain oxygen, either in the form of a ketocarbonyl or an ester group. The remaining structures include 13-nitrotridecanoic acid and three unsaturated, fourteen carbon carboxylic acids. 9-Tetradecynoic acid was the most potent anti-trypanosomal agent identified among the 247 compounds screened.

Cells Used for Growth Assays

For toxicity assays, cloned *T. brucei* (strain 427) of variant antigen type 221 (obtained from G.A.M. Cross, Rockefeller University) were harvested from CD-1 mice at a parasitemia of $2$–$5 \times 10^8$ trypanosomes/mL. After centrifugation of the infected blood (430 x g; 8 min; 4° C.), the upper portion of the buffy coat was retained, with care taken to avoid contamination with erythrocytes. This material, consisting predominantly of trypanosomes, was then resuspended in BBS containing 1 mg/mL fatty acid free bovine serum albumin. The suspension was centrifuged (3,000 x g; 8 min; 4° C.), and the cell pellet resuspended in culture medium to a final density of $1.5 \times 10^7$ cells/mL. (The composition of this culture medium was as described above except that 40 μM monothioglycerol was added; Duszenko et al., 1985; Doering et al., 1990; Hamm et al., 1990.) The doubling time of trypanosomes under these culture conditions is approximately 6 h at 37° C.

Growth Assay

This rapid assay, which can accommodate multiple samples, depends on measurement of the color change produced in the medium's phenol red indicator dye due to acidification by growing trypanosomes. Stocks of analogs (10 mM in absolute ethanol, identified only by a code number) were diluted in culture medium to twice the concentration to be tested. Aliquots of 100 μL were dispensed into 96-well microtiter plates and warmed to 37° C. in a 5% $CO_2$ incubator before the addition of an equal volume of cell suspension ($1.5 \times 10^7$/mL, see above). All assays were performed in quadruplicate in each plate. Control wells included appropriately diluted ethanol (which had no effect on cell growth) and 10 μM 11-oxatetradecanoic acid. The plate was incubated for 36 h at 37° C. and then stored at 4° C. for 12 h to allow equilibration of $CO_2$ in the medium with that in air. The absorbance of each sample, at 550 nm and 405 nm (values chosen based on the absorption spectra of fresh and acidified media), was then read in a $UV_{max}$ kinetic microplate reader (Molecular Devices). To control for any variation in sample volume, the ratio of absorbance at 550 nm to absorbance at 405 nm for each well was calculated. This ratio was then averaged for each quadruplicate set and normalized to the average obtained in the set of control wells containing 10 μM 11-oxatetradecanoic acid, yielding an "efficacy value".

TABLE 2

| Structure | Reference | Efficacy | Group[1] |
|---|---|---|---|
| Saturated Fatty Acids[2] | | | |
| $CH_3$—$(CH_2)_6$—COOH | | | 1 |
| $CH_3$—$(CH_2)_8$—COOH | | | 1 |
| $CH_3$—$(CH_2)_{10}$—COOH | | | 1 |
| $CH_3$—$(CH_2)_{11}$—COOH | | | 1 |
| $CH_3$—$(CH_2)_{12}$—COOH | | | 1 |
| $CH_3$—$(CH_2)_{13}$—COOH | | | 1 |
| $CH_3$—$(CH_2)_{14}$—COOH | | | 1 |
| $CH_3$—$(CH_2)_{16}$—COOH | | | 1 |
| $CH_3$—$(CH_2)_{18}$—COOH | | | 1 |
| Oxatetradecanoic acids | | | |
| $CH_3$—O—$(CH_2)_{11}$—COOH | Kishore et al., 1991 | | 2 |
| $CH_3$—$CH_2$—O—$(CH_2)_{10}$—COOH | Kishore et al., 1991 | | 1 |
| $CH_3$—$(CH_2)_2$—O—$(CH_2)_9$—COOH | Kishore et al., 1991 | | 3*[3] |
| $CH_3$—$(CH_2)_3$—O—$(CH_2)_8$—COOH | Kishore et al., 1991 | | 3* |
| $CH_3$—$(CH_2)_5$—O—$(CH_2)_6$—COOH | Kishore et al., 1991 | | 3b |
| $CH_3$—$(CH_2)_6$—O—$(CH_2)_5$—COOH | Kishore et al., 1991 | | 3**[4] |
| $CH_3$—$(CH_2)_7$—O—$(CH_2)_4$—COOH | Kishore et al., 1991 | | 1 |
| $CH_3$—$(CH_2)_8$—O—$(CH_2)_3$—COOH | Kishore et al., 1991 | | 3* |
| $CH_3$—$(CH_2)_9$—O—$(CH_2)_2$—COOH | Kishore et al., 1991 | | 2 |
| $CH_3$—$(CH_2)_{10}$—O—$CH_2$—COOH | Kishore et al., 1991 | | 1 |
| Thiatetradecanoic acids | | | |
| $CH_3$—S—$(CH_2)_{11}$—COOH | Kishore et al., 1991 | | 3* |
| $CH_3$—$CH_2$—S—$(CH_2)_{10}$—COOH | Kishore et al., 1991 | | 2 |
| $CH_3$—$(CH_2)_3$—S—$(CH_2)_8$—COOH | Kishore et al., 1991 | | 2 |
| $CH_3$—$(CH_2)_4$—S—$(CH_2)_7$—COOH | Kishore et al., 1991 | | 3b* |
| $CH_3$—$(CH_2)_5$—S—$(CH_2)_6$—COOH | Kishore et al., 1991 | | 2 |
| $CH_3$—$(CH_2)_6$—S—$(CH_2)_5$—COOH | Kishore et al., 1991 | | 3** |
| $CH_3$—$(CH_2)_7$—S—$(CH_2)_4$—COOH | Kishore et al., 1991 | | 2a |
| $CH_3$—$(CH_2)_8$—S—$(CH_2)_3$—COOH | Kishore et al., 1991 | | 3** |
| $CH_3$—$(CH_2)_9$—S—$(CH_2)_2$—COOH | Kishore et al., 1991 | | 1 |
| $CH_3$—$(CH_2)_{10}$—S—$CH_2$—COOH | Kishore et al., 1991 | | 1 |
| Myristic acid analogs containing sulfur and/or oxygen substituents | | | |
| $CH_3$—$CH_2$—S—$(CH_2)_5$—S—$(CH_2)_4$—COOH | Kishore et al., 1991 | | 1 |

TABLE 2-continued

| Structure | Reference | Efficacy | Group[1] |
|---|---|---|---|
| $CH_3-CH_2-S-(CH_2)_2-O-(CH_2)_7-COOH$ | Kishore et al., 1991 | | 2 |
| $CH_3-CH_2-O-(CH_2)_2-S-(CH_2)_7-COOH$ | Kishore et al., 1991 | | 1 |
| $CH_3-CH_2-O-(CH_2)_5-S-(CH_2)_4-COOH$ | Kishore et al., 1991 | | 1 |
| $CH_3-O-(CH_2)_2-O-(CH_2)_2-O-(CH_2)_5-COOH$ | Kishore et al., 1991 | | 1 |
| Oxotetradecanoic acids | | | |
| $CH_3-CO-(CH_2)_{11}-COOH$ | Devadas et al., 1992 | | 2 |
| $CH_3-CH_2-CO-(CH_2)_{10}-COOH$ | Devadas et al., 1992 | | 1 |
| $CH_3-(CH_2)_2-CO-(CH_2)_9-COOH$ | Devadas et al., 1992 | | 2a* |
| $CH_3-(CH_2)_3-CO-(CH_2)_8-COOH$ | Devadas et al., 1992 | | 2b |
| $CH_3-(CH_2)_4-CO-(CH_2)_7-COOH$ | Devadas et al., 1992 | | 2a* |
| $CH_3-(CH_2)_5-CO-(CH_2)_6-COOH$ | Devadas et al., 1992 | | 1 |
| $CH_3-(CH_2)_6-CO-(CH_2)_5-COOH$ | Devadas et al., 1992 | | 3** |
| $CH_3-(CH_2)_7-CO-(CH_2)_4-COOH$ | Devadas et al., 1992 | | 1 |
| $CH_3-(CH_2)_8-CO-(CH_2)_3-COOH$ | Devadas et al., 1992 | | 3b* |
| $CH_3-(CH_2)_9-CO-(CH_2)_2-COOH$ | Devadas et al., 1992 | | 2 |
| $CH_3-(CH_2)_{10}-CO-CH_2-COOH$ | Devadas et al., 1992 | | 1 |
| Myristic acid analogs containing ester groups | | | |
| $CH_3-O-CO-(CH_2)_{10}-COOH$ | Devadas et al., 1992 | | 2 |
| $CH_3-CH_2-O-CO-(CH_2)_9-COOH$ | Devadas et al., 1992 | | 1 |
| $CH_3-(CH_2)_2-O-CO-(CH_2)_8-COOH$ | Devadas et al., 1992 | | 2 |
| $CH_3-(CH_2)_3-O-CO-(CH_2)_7-COOH$ | Devadas et al., 1992 | | 2a |
| $CH_3-(CH_2)_4-O-CO-(CH_2)_6-COOH$ | Devadas et al., 1992 | | 1a |
| $CH_3-(CH_2)_5-O-CO-(CH_2)_5-COOH$ | Devadas et al., 1992 | | 2b |
| $CH_3-(CH_2)_6-O-CO-(CH_2)_4-COOH$ | Devadas et al., 1992 | | 2 |
| $CH_3-(CH_2)_7-O-CO-(CH_2)_3-COOH$ | Devadas et al., 1992 | | 3 |
| $CH_3-(CH_2)_8-O-CO-(CH_2)_2-COOH$ | Devadas et al., 1992 | | 3b* |
| $CH_3-(CH_2)_9-O-CO-CH_2-COOH$ | Devadas et al., 1992 | | 1 |
| $CH_3-(CH_2)_{10}-O-CO-(CH_2)_{10}-COOH$ | Devadas et al., 1992 | | 1 |
| Myristic acid analogs containing amide groups | | | |
| $CH_3-NH-CO-(CH_2)_{10}-COOH$ | Devadas et al., 1992 | | 1 |
| $CH_3-(CH_2)_2-NH-CO-(CH_2)_8-COOH$ | Devadas et al., 1992 | | 1 |
| $CH_3-(CH_2)_3-NH-CO-(CH_2)_7-COOH$ | Devadas et al., 1992 | | 1 |
| $CH_3-(CH_2)_4-NH-CO-(CH_2)_6-COOH$ | Devadas et al., 1992 | | 1 |
| $CH_3-(CH_2)_5-NH-CO-(CH_2)_5-COOH$ | Devadas et al., 1992 | | 1 |
| $CH_3-(CH_2)_6-NH-CO-(CH_2)_4-COOH$ | Devadas et al., 1992 | | 1 |
| $CH_3-(CH_2)_7-NH-CO-(CH_2)_3-COOH$ | Devadas et al., 1992 | | 1 |
| $CH_3-(CH_2)_8-NH-CO-(CH_2)_2-COOH$ | Devadas et al., 1992 | | 1 |
| $CH_3-(CH_2)_9-NH-CO-CH_2-COOH$ | Devadas et al., 1992 | | 1 |
| Myristic acid analogs containing acylamino amide groups | | | |
| $CH_3-CO-NH-(CH_2)_{10}-COOH$ | Devadas et al., 1992 | | 1 |
| $CH_3-(CH_2)_3-CO-NH-(CH_2)_7-COOH$ | Devadas et al., 1992 | | 1 |
| $CH_3-(CH_2)_4-CO-NH-(CH_2)_6-COOH$ | Devadas et al., 1992 | | 1 |
| $CH_3-(CH_2)_5-CO-NH-(CH_2)_5-COOH$ | Devadas et al., 1992 | | 1 |
| $CH_3-(CH_2)_6-CO-NH-(CH_2)_4-COOH$ | Devadas et al., 1992 | | 1 |
| $CH_3-(CH_2)_7-CO-NH-(CH_2)_3-COOH$ | Devadas et al., 1992 | | 1 |
| $CH_3-(CH_2)_8-CO-NH-(CH_2)_2-COOH$ | Devadas et al., 1992 | | 1 |
| $CH_3-(CH_2)_9-CO-NH-CH_2-COOH$ | Devadas et al., 1992 | | 1a |
| Nitroalkylcarboxylic acids | | | |
| $O_2N-(CH_2)_9-COOH$ | Lu et al., 1994[5] | | 1 |
| $O_2N-(CH_2)_{10}-COOH$ | Lu et al., 1994 | | 2a |
| $O_2N-(CH_2)_{12}-COOH$ | Lu et al., 1994 | | 3 |
| Halogenated analogs | | | |
| $Br-(CH_2)_{12}-COOH$ | Lu et al., 1994 | | 2 |
| $Br-(CH_2)_{13}-COOH$ | Lu et al., 1994 | | 2 |
| $F_3C-(CH_2)_{12}-COOH$ | Lu et al., 1994 | | 1 |
| $F_3C-CH=CH-(CH_2)_{10}COOH$ | Lu et al., 1994 | | 1 |
| Tetradecenoic acids | | | |
| $CH_2=CH-(CH_2)_{11}-COOH$ | Kishore et al., 1991 | | 1 |
| $CH_3-CH=CH-(CH_2)_{10}-COOH$ | Kishore et al., 1991 | Z12[6] | 1 |
| $CH_3-CH_2-CH=CH-(CH_2)_9-COOH$ | Kishore et al., 1991 | Z11 | 2b |
| $CH_3-(CH_2)_2-CH=CH-(CH_2)_8-COOH$ | Kishore et al., 1991 | Z10 | 1 |
| $CH_3-(CH_2)_4-CH=CH-(CH_2)_6-COOH$ | Kishore et al., 1991 | Z8 | 1a |
| $CH_3-(CH_2)_5-CH=CH-(CH_2)_5-COOH$ | Kishore et al., 1991 | Z7 | 2b |
| $CH_3-(CH_2)_5-CH=CH-(CH_2)_5-COOH$ | Kishore et al., 1991 | E7[7] | 1 |
| $CH_3-(CH_2)_6-CH=CH-(CH_2)_4-COOH$ | Kishore et al., 1991 | E6 | 2b |
| $CH_3-(CH_2)_6-CH=CH-(CH_2)_4-COOH$ | Kishore et al., 1991 | Z6 | 1 |
| Isomer mixture: 15% E6, 85% Z6 | Kishore et al., 1991 | E:Z6 | 1 |
| $CH_3-(CH_2)_7-CH=CH-(CH_2)_3-COOH$ | Kishore et al., 1991 | E5 | 1 |
| $CH_3-(CH_2)_7-CH=CH-(CH_2)_3-COOH$ | Kishore et al., 1991 | Z5 | 1 |
| $CH_3-(CH_2)_8-CH=CH-(CH_2)_2-COOH$ | Kishore et al., 1991 | Z4 | 1 |

TABLE 2-continued

| Structure | Reference | Efficacy | Group[1] |
|---|---|---|---|
| $CH_3$—$(CH_2)_8$—$CH=CH$—$(CH_2)_2$—$COOH$ | Kishore et al., 1991 | E4 | 1 |
| $CH_3$—$(CH_2)_9$—$CH=CH$—$CH_2$—$COOH$ | Kishore et al., 1991 | Z3 | 1 |
| $CH_3$—$(CH_2)_{10}$—$CH=CH$—$COOH$ | Kishore et al., 1991 | E2 | 1 |
| $CH_3$—$(CH_2)_{10}$—$CH=CH$—$COOH$ | Kishore et al., 1991 | Z2 | 1 |
| $CH_3$—$CH_2$—$CH=CH$—$(CH_2)_3$—$COOH$ | Rudnick et al., 1992 | C8:Z5 | 1 |
| $CH_3$—$(CH_2)_3$—$CH=CH$—$(CH_2)_3$—$COOH$ | Rudnick et al., 1992 | C10:Z5 | 1 |
| $CH_3$—$(CH_2)_5$—$CH=CH$—$(CH_2)_3$—$COOH$ | Rudnick et al., 1992 | C12:Z5 | 1 |
| $CH_3$—$(CH_2)_{10}$—$CH=CH$—$(CH_2)_2$—$COOH$ | Rudnick et al., 1992 | C16:Z4 | 1 |
| $CH_3$—$(CH_2)_9$—$CH=CH$—$(CH_2)_3$—$COOH$ | Rudnick et al., 1992 | C16:Z5 | 1 |
| $CH_3$—$(CH_2)_8$—$CH=CH$—$(CH_2)_4$—$COOH$ | Rudnick et al., 1992 | C16:Z6 | 1 |
| $CH_3$—$(CH_2)_{10}$—$CH=CH$—$(CH_2)_3$—$COOH$ | Rudnick et al., 1992 | C17:Z5 | 1 |
| $CH_3$—$(CH_2)_{11}$—$CH=CH$—$(CH_2)_3$—$COOH$ | Rudnick et al., 1992 | C18:Z5 | 1 |
| Tetradecadienoic acids | | | |
| $CH_3$—$(CH_2)_2$—$CH=CH$—$CH=CH$—$(CH_2)_6$—$COOH$ | See Examples | | 1 |
| $CH_3$—$(CH_2)_4$—$CH=CH$—$CH=CH$—$(CH_2)_4$—$COOH$ | See Examples | | 2b |
| $CH_3$—$(CH_2)_5$—$CH=CH$—$CH=CH$—$(CH_2)_3$—$COOH$ | See Examples | | 3 |
| Tetradecynoic acids | | | |
| $HC\equiv C$—$(CH_2)_{11}$—$COOH$ | Kishore et al., 1991 | | 2b |
| $CH_3$—$C\equiv C$—$(CH_2)_{10}$—$COOH$ | Kishore et al., 1991 | | 1 |
| $CH_3CH_2$—$C\equiv C$—$(CH_2)_9$—$COOH$ | Kishore et al., 1991 | | 1 |
| $CH_3$—$(CH_2)_2$—$C\equiv C$—$(CH_2)_8$—$COOH$ | Kishore et al., 1991 | | 2 |
| $CH_3$—$(CH_2)_3$—$C\equiv C$—$(CH_2)_7$—$COOH$ | Kishore et al., 1991 | | 3a |
| $CH_3$—$(CH_2)_4$—$C\equiv C$—$(CH_2)_6$—$COOH$ | Kishore et al., 1991 | | 3 |
| $CH_3$—$(CH_2)_5$—$C\equiv C$—$(CH_2)_5$—$COOH$ | Kishore et al., 1991 | | 2 |
| $CH_3$—$(CH_2)_6$—$C\equiv C$—$(CH_2)_4$—$COOH$ | Kishore et al., 1991 | | 2 |
| $CH_3$—$(CH_2)_7$—$C\equiv C$—$(CH_2)_3$—$COOH$ | Kishore et al., 1991 | | 2 |
| $CH_3$—$(CH_2)_8$—$C\equiv C$—$(CH_2)_2$—$COOH$ | Kishore et al., 1991 | | 1 |
| $CH_3$—$(CH_2)_9$—$C\equiv C$—$CH_2$—$COOH$ | Kishore et al., 1991 | | 1 |
| $CH_3$—$(CH_2)_{10}$—$C\equiv C$—$COOH$ | Kishore et al., 1991 | | 1 |
| $CH_3$—$(CH_2)_7$—$C\equiv C$—$(CH_2)_2$—$COOH$ | Rudnick et al., 1992 | C13:Y4[8] | 1 |
| $CH_3$—$(CH_2)_6$—$C\equiv C$—$(CH_2)_3$—$COOH$ | Rudnick et al., 1992 | C13:Y5 | 1 |
| $CH_3$—$(CH_2)_5$—$C\equiv C$—$(CH_2)_4$—$COOH$ | Rudnick et al., 1992 | C13:Y6 | 2b |
| $CH_3$—$(CH_2)_9$—$C\equiv C$—$(CH_2)_2$—$COOH$ | Rudnick et al., 1992 | C15:Y4 | 1 |
| $CH_3$—$(CH_2)_8$—$C\equiv C$—$(CH_2)_3$—$COOH$ | Rudnick et al., 1992 | C15:Y5 | 1 |
| $CH_3$—$(CH_2)_7$—$C\equiv C$—$(CH_2)_4$—$COOH$ | Rudnick et al., 1992 | C15:Y6 | 1 |
| $CH_3$—$(CH_2)_{10}$—$C\equiv C$—$(CH_2)_2$—$COOH$ | Rudnick et al., 1992 | C16:Y4 | 1 |
| $CH_3$—$(CH_2)_9$—$C\equiv C$—$(CH_2)_3$—$COOH$ | Rudnick et al., 1992 | C16:Y5 | 1 |
| $CH_3$—$(CH_2)_8$—$C\equiv C$—$(CH_2)_4$—$COOH$ | Rudnick et al., 1992 | C16:Y6 | 1 |
| Aromatic analogs | | | |
| 11 Carbon Equivalent Length[9] | | | |
| $C_6H_5$—$(CH_2)_7$—$COOH$ | Kishore et al., 1991 | | 2b |
| $C_6H_5$—$(CH_2)_2$—$CH=CH$—$(CH_2)_3$—$COOH$ | Kishore et al., 1991 | | 1 |
| 12 Carbon Equivalent Length | | | |
| $C_6H_5$—$(CH_2)_8$—$COOH$ | Kishore et al. 1991 | | 1 |
| $C_6H_5$—$CH=CH$—$(CH_2)_6$—$COOH$ | Kishore et al., 1991 | | 1a |
| $C_6H_5$—$(CH_2)_2$—$CH=CH$—$(CH_2)_4$—$COOH$ | Kishore et al., 1991 | | 1 |
| $C_6H_5$—$O$—$(CH_2)_7$—$COOH$ | See Examples | | 1 |
| 13 Carbon Equivalent Length | | | |
| $C_6H_5$—$(CH_2)_9$—$COOH$ | Kishore et al., 1991 | | 2b |
| $CH_3$—$C_6H_4$—$(CH_2)_8$—$COOH$ | Kishore et al., 1991 | | 1 |
| $CH_3$—$CH_2$—$C_6H_4$—$(CH_2)_7$—$COOH$ | Kishore et al., 1991 | | 2b |
| $CH_3$—$(CH_2)_2$—$C_6H_4$—$(CH_2)_6$—$COOH$ | Kishore et al., 1991 | | 1 |
| $CH_3$—$(CH_2)_3$—$C_6H_4$—$(CH_2)_5$—$COOH$ | Kishore et al., 1991 | | 1 |
| $CH_3$—$(CH_2)_4$—$C_6H_4$—$(CH_2)_4$—$COOH$ | Gokel, et al., 1992 | | 1 |
| $CH_3$—$(CH_2)_5$—$C_6H_4$—$(CH_2)_3$—$COOH$ | Gokel, et al., 1992 | | 1a |
| $CH_3$—$(CH_2)_6$—$C_6H_4$—$(CH_2)_2$—$COOH$ | Gokel, et al., 1992 | | 1 |
| $C_6H_5$—$CH_2$—$CH=CH$—$(CH_2)_6$—$COOH$ | Kishore et al., 1991 | | 1 |
| $CH_3$—$C_6H_4$—$CH=CH$—$(CH_2)_6$—$COOH$ | Kishore et al., 1991 | | 1 |
| $CH_3$—$CH_2$—$C_6H_4$—$CH=CH$—$(CH_2)_5$—$COOH$ | Kishore et al., 1991 | | 1 |
| $CH_3$—$(CH_2)_2$—$C_6H_4$—$CH=CH$—$(CH_2)_4$—$COOH$ | Kishore et al., 1991 | | 1 |
| $CH_3$—$(CH_2)_3$—$C_6H_4$—$CH=CH$—$(CH_2)_3$—$COOH$ | Kishore et al., 1991 | | 1 |
| $CH_3$—$(CH_2)_4$—$C_6H_4$—$CH=CH$—$(CH_2)_2$—$COOH$ | Gokel, et al., 1992 | | 1 |
| $CH_3$—$(CH_2)_5$—$C_6H_4$—$CH=CH$—$CH_2$—$COOH$ | Gokel, et al., 1992 | | 1 |
| $CH_3$—$(CH_2)_6$—$C_6H_4$—$CH=CH$—$COOH$ | Gokel, et al., 1992 | | 1 |
| $CH_3$—$O$—$C_6H_4$—$(CH_2)_7$—$COOH$ | See Examples | | 1 |
| $CH_3$—$CH_2$—$O$—$C_6H_4$—$(CH_2)_6$—$COOH$ | See Examples | | 1 |
| $CH_3$—$(CH_2)_2$—$O$—$C_6H_4$—$(CH_2)_5$—$COOH$ | See Examples | | 1 |
| $CH_3$—$(CH_2)_3$—$O$—$C_6H_4$—$(CH_2)_4$—$COOH$ | Gokel, et al. 1992 | | 3 |
| $CH_3$—$(CH_2)_4$—$O$—$C_6H_4$—$(CH_2)_3$—$COOH$ | Gokel, et al., 1992 | | 1 |
| $CH_3$—$(CH_2)_5$—$O$—$C_6H_4$—$(CH_2)_2$—$COOH$ | Gokel, et al., 1992 | | 1 |
| $CH_3$—$O$—$C_6H_4$—$CH=CH$—$(CH_2)_5$—$COOH$ | See Examples | | 1 |

TABLE 2-continued

| Structure | Reference | Efficacy | Group[1] |
|---|---|---|---|
| $CH_3-CH_2-O-C_6H_4-CH=CH-(CH_2)_4-COOH$ | See Examples | | 1 |
| $CH_3-(CH_2)_2-O-C_6H_4-CH=CH-(CH_2)_3-COOH$ | See Examples | | 1 |
| $CH_3-(CH_2)_3-O-C_6H_4-CH=CH-(CH_2)_2-COOH$ | Gokel, et al., 1992 | | 1 |
| $CH_3-(CH_2)_4-O-C_6H_4-CH=CH-CH_2-COOH$ | Gokel, et al., 1992 | | 1 |
| $CH_3-(CH_2)_5-O-C_6H_4-CH=CH-COOH$ | Gokel, et al., 1992 | | 1 |
| $C_6H_5-O-(CH_2)_8-COOH$ | See Examples | | 1 |
| $C_6H_5-S-(CH_2)_8-COOH$ | See Examples | | 1 |
| $C_6H_5-CH_2-O-(CH_2)_7-COOH$ | See Examples | | 1 |
| $C_6H_5-CH_2-S-(CH_2)_7-COOH$ | See Examples | | 1 |
| 14 Carbon Equivalent Length | | | |
| $C_6H_5-(CH_2)_{10}-COOH$ | Heuckeroth et al., 1990 | | 2b |
| $CH_3-C_6H_4-(CH_2)_9-COOH$ | Kishore et al., 1991 | | 1 |
| $CH_3-CH_2-C_6H_4-(CH_2)_8-COOH$ | Kishore et al., 1991 | | 1a |
| $CH_3-(CH_2)_2-C_6H_4-(CH_2)_7-COOH$ | See Examples | | 1 |
| $CH_3-(CH_2)_3-C_6H_4-(CH_2)_6-COOH$ | See Examples | | 1 |
| $CH_3-(CH_2)_4-C_6H_4-(CH_2)_5-COOH$ | See Examples | | 1 |
| $CH_3-(CH_2)_5-C_6H_4-(CH_2)_4-COOH$ | Gokel, et al., 1992 | | 1 |
| $CH_3-(CH_2)_6-C_6H_4-(CH_2)_3-COOH$ | Gokel, et al., 1992 | | 1 |
| $C_6H_5-(CH_2)_2-CH=CH-(CH_2)_6-COOH$ | Heuckeroth et al., 1990 | | 1 |
| $CH_3-C_6H_4-CH=CH-(CH_2)_7-COOH$ | Kishore et al., 1991 | | 1 |
| $CH_3-CH_2-C_6H_4-CH=CH-(CH_2)_6-COOH$ | Kishore et al., 1991 | | 1 |
| $CH_3-(CH_2)_2-C_6H_4-CH=CH-(CH_2)_5-COOH$ | See Examples | | 1 |
| $CH_3-(CH_2)_3-C_6H_4-CH=CH-(CH_2)_4-COOH$ | See Examples | | 1 |
| $CH_3-(CH_2)_4-C_6H_4-CH=CH-(CH_2)_3-COOH$ | See Examples | | 1 |
| $CH_3-(CH_2)_5-C_6H_4-CH=CH-(CH_2)_2-COOH$ | Gokel, et al., 1992 | | 1 |
| $CH_3-(CH_2)_6-C_6H_4-CH=CH-CH_2-COOH$ | Gokel, et al., 1992 | | 1 |
| $CH_3-O-C_6H_4-(CH_2)_8-COOH$ | Kishore et al., 1991 | | 1a |
| $CH_3-CH_2-O-C_6H_4-(CH_2)_7-COOH$ | Kishore et al., 1991 | | 1a |
| $CH_3-(CH_2)_2-O-C_6H_4-(CH_2)_6-COOH$ | See Examples | | 1 |
| $CH_3-(CH_2)_3-O-C_6H_4-(CH_2)_5-COOH$ | See Examples | | 1 |
| $CH_3$$-(CH_2)_4-O-C_6H_4-(CH_2)_4-COOH$ | Gokel et al., 1992 | | 3 |
| $CH_3-(CH_2)_5-O-C_6H_4-(CH_2)_3-COOH$ | Gokel et al., 1992 | | 1 |
| $CH_3-(CH_2)_6-O-C_6H_4-(CH_2)_2-COOH$ | Gokel et al., 1992 | | 1 |
| $CH_3-O-C_6H_4-CH=CH-(CH_2)_6-COOH$ | Kishore et al., 1991 | | 1 |
| $CH_3-CH_2-O-C_6H_4-CH=CH-(CH_2)_5-COOH$ | Kishore et al., 1991 | | 1a |
| $CH_3-(CH_2)_2-O-C_6H_4-CH=CH-(CH_2)_4-COOH$ | See Examples | | 1 |
| $CH_3-(CH_2)_3-O-C_6H_4-CH=CH-(CH_2)_3-COOH$ | See Examples | | 2a |
| $CH_3-(CH_2)_4-O-C_6H_4-CH=CH-(CH_2)_2-COOH$ | Gokel et al., 1992 | | 2 |
| $CH_3-(CH_2)_5-O-C_6H_4-CH=CH-CH_2-COOH$ | Gokel et al., 1992 | | 1 |
| $CH_3-(CH_2)_6-O-C_6H_4-CH=CH-COOH$ | Gokel et al., 1992 | | 1 |
| $C_6H_5-O-(CH_2)_9-COOH$ | Kishore et al., 1991 | | 1 |
| $C_6H_5-S-(CH_2)_9-COOH$ | Kishore et al., 1991 | | 1 |
| $CH_3-C_6H_4-O-(CH_2)_8-COOH$ | Kishore et al., 1991 | | 1 |
| $CH_3-C_6H_4-S-(CH_2)_8-COOH$ | Kishore et al., 1991 | | 1 |
| $CH_3-S-C_6H_4-(CH_2)_8-COOH$ | Kishore et al., 1991 | | 1 |
| $CH_3-S-C_6H_4-CH=CH-(CH_2)_6-COOH$ | Kishore et al., 1991 | | 1 |
| $CH_3-CH_2-C_6H_4-O-(CH_2)_7-COOH$ | See Examples | | 1 |
| 15 Carbon Equivalent Length | | | |
| $C_6H_5-(CH_2)_{11}-COOH$ | Rapoport and Newman, 1947 | | 1 |
| $C_6H_5-CH=CH-(CH_2)_9-COOH$ | See Examples | | 1 |
| $C_6H_5-O-(CH_2)_{10}-COOH$ | See Examples | | 1 |
| Azido-aromatic analogs | | | |
| $p-N_3-C_6H_4-(CH_2)_6-COOH$ | Lu et al., 1994[5] | | 1 |
| $p-N_3-C_6H_4-(CH_2)_7-COOH$ | Lu et al., 1994 | | 1b |
| $p-N_3-C_6H_4-(CH_2)_8-COOH$ | Lu et al., 1994 | | 1 |
| $m-N_3-C_6H_4-(CH_2)_8-COOH$ | Lu et al., 1994 | | 1 |
| $m-N_3-C_6H_4-(CH_2)_{10}-COOH$ | Lu et al., 1994 | | 1b |
| $p-N_3-C_6H_4-O-(CH_2)_5-COOH$ | Lu et al., 1994 | | 1b |
| $m-N_3-C_6H_4-O-(CH_2)_5-COOH$ | Lu et al., 1994 | | 1 |
| $p-N_3-C_6H_4-O-(CH_2)_6-COOH$ | Lu et al., 1994 | | 1b |
| $m-N_3-C_6H_4-O-(CH_2)_6-COOH$ | Lu et al., 1994 | | 1 |
| $p-N_3-C_6H_4-O-(CH_2)_7-COOH$ | Lu et al., 1994 | | 1 |
| $m-N_3-C_6H_4-O-(CH_2)_7-COOH$ | Lu et al., 1994 | | 1 |
| Nitro-aromatic analogs | | | |
| $O_2N-C_6H_4-CH=CH-(CH_2)_6-COOH$ | Lu et al., 1994 | | 1 |
| $O_2N-C_6H_4-CH=CH-(CH_2)_5-COOH$ | Lu et al., 1994 | | 1a |
| $O_2N-C_6H_4-CH=CH-(CH_2)_4-COOH$ | Lu et al., 1994 | | 1 |
| $H_2N-C_6H_4-(CH_2)_6-COOH$ | Lu et al., 1994 | | 1 |
| $H_2N-C_6H_4-(CH_2)_7-COOH$ | Lu et al., 1994 | | 1 |
| Halo-aromatic analogs | | | |
| $o-F-C_6H_4-(CH_2)_8-COOH$ | Lu et al., 1994 | | 1 |
| $m-F-C_6H_4-(CH_2)_8-COOH$ | Lu et al., 1994 | | 1 |

TABLE 2-continued

| Structure | Reference | Efficacy | Group[1] |
|---|---|---|---|
| p-F—C[6]H[4]—(CH[2])[8]—COOH | Lu et al., 1994 | | 1a |
| p-Cl—C[6]H[4]—(CH[2])[8]—COOH | Lu et al., 1994 | | 1 |
| p-Br—C[6]H[4]—(CH[2])[8]—COOH | Lu et al., 1994 | | 1a |
| p-CF[3]—C[6]H[4]—(CH[2])[8]—COOH | Lu et al., 1994 | | 1 |
| o-F—C[6]H[4]—CH=C—(CH[2])[6]—COOH | Lu et al., 1994 | | 1 |
| m-F—C[6]H[4]—CH=CH—(CH[2])[6]—COOH | Lu et al., 1994 | | 1 |
| p-F—C[6]H[4]—CH=CH—(CH[2])[6]—COOH | Lu et al., 1994 | | 1a |
| p-Cl—C[6]H[4]—CH=CH—(CH[2])[6]—COOH | Lu et al., 1994 | | 1 |
| p-Br—C[6]H[4]—CH=CH—(CH[2])[6]—COOH | Lu et al., 1994 | | 1 |
| p-CF[3]—C[6]H[4]—CH=CH—(CH[2])[6]—COOH | Lu et al., 1994 | | 1 |
| Hetero-aromatic analogs | | | |
| CH[3]—(CH[2])[7]—furyl-(CH[2])[2]—COOH | Rudnick et al., 1992 | | 1 |
| CH[3]—(CH[2])[6]—furyl-(CH[2])[3]—COOH | Rudnick et al., 1992 | | 2 |
| CH[3]—(CH[2])[5]—furyl-(CH[2])[4]—COOH | Rudnick et al., 1992 | | 3 |
| CH[3]—(CH[2])[4]—furyl-(CH[2])[5]—COOH | Rudnick et al., 1992 | | 2b |
| 2-Furyl-(CH[2])[8]—COOH | See Examples | | 1 |
| [2-(5-CH[3]-furyl)]-(CH[2])[8]—COOH | See Examples | | 1 |
| 2-Furyl-(CH[2])[10]—COOH | See Examples | | 2b |
| 2-Furyl-CH=CH—(CH[2])[6]—COOH | See Examples | | 1 |
| [2-(5-CH[3]-furyl)][-CH=CH—(CH[2])[2])[6]—COOH | See Examples | | 1 |
| 2-Furyl-CH=CH—(CH[2])[8]—COOH | See Examples | | 1 |
| 2-Furyl-CH=CH—(CH[2])[9]—COOH | See Examples | | 1 |
| 2-Thienyl-(CH[2])[8]—COOH | See Examples | | 1a |
| 2-Thienyl-(CH[2])[9]—COOH | Kishore et al., 1991 | | 1 |
| [2-(5-CH[3]-thienyl)]-(CH[2])[8]—COOH | See Examples | | 1 |
| 2-Thienyl-(CH[2])[10]—COOH | See Examples | | 2b |
| 2-Thienyl-CH=CH—(CH[2])[6]—COOH | See Examples | | 1 |
| [2-(5-CH[3]-thienyl)]-CH=CH—(CH[2])[6]—COOH | See Examples | | 1 |
| 2-Thienyl-CH=CH—(CH[2])[8]—COOH | See Examples | | 1 |

[1]Efficacy groups were assigned as described in Methods and the text. Subgroup "a" indicates compounds near the upper boundary of an efficacy group; subgroup "b" indicates compounds at the lower boundary. The 20 most toxic compounds (Group 3) are highllghted in bold type.
[2]Purchased from Nu Chek Prep, Inc. (Elysian, MN)
[3]*Indicates compounds that were categorized as group 2 when tested at 2 μM.
[4]**Indicates compounds that remained in group 3 when tested at 2 μM.
[5]T. Lu, Q. Li, A. Katoh, J. Hernandez, K. Duffin, E. Jackson-Machelski, L. J. Knoll, G. W. Gokel, and J. I. Gordon, J. Biol. Chem., 269, 5346–5357 (1994).
[6]Z, designates cis double bond geometry
[7]E, designates trans double bond geometry
[8]Y, indicates triple bond
[9]Examination of CPK space filling atomic models indicates that the width of an aromatic ring is equivalent to three methylenes.

The antiparasitic agents described herein can be used for administration to mammalian hosts infected with trypanosomes and the like by conventional means, preferably in formulations with pharmaceutically acceptable diluents and carriers. The amount of the active agent to be administered must be an effective amount, that is, an amount which is medically beneficial but does not present toxic effects which overweigh the advantages which accompany its use. It would be expected that the adult human dosage would normally range upward from about one milligram of the active compound. A suitable route of administration is orally in the form of capsules, tablets, syrups, elixirs and the like, although parenteral administration also can be used. Appropriate formulations of the active compound in pharmaceutically acceptable diluents and carriers in therapeutic dosage form can be prepared by reference to general texts in the field such as, for example, *Remington's Pharmaceutical Sciences,* Ed. Arthur Osol, 16th ed., 1980, Mack Publishing Co., Easton, Pa.

Various other examples will be apparent to the person skilled in the art after reading the present disclosure without departing from the spirit and scope of the invention. All such other examples are intended to be included within the scope of the appended claims.

REFERENCES

Bryant, M. L., Heuckeroth, R. O., Kimata, J. T., Ratner, L., and Gordon, J. I. (1989) Proc. Natl. Acad. Sci. USA 86, 8655–8659.

Bryant, M. L., Ratner, L., Duronio, R. J., Kishore, N. S., Adams, S. P., and Gordon, J. I. (1991) Proc. Natl. Acad. Sci. USA 88, 2055–2059.

Devadas, B., Adams, S. P., and Gordon, J. I. (1991) J. Lab. Comp. Radiopharm. 29, 157–164.

Devadas, B., Lu, T., Katoh, A., Kishore, N. S., Wade, A. C., Mehta, P. P., Rudnick, D. A., Bryant, M. L., Adams,, S. P., Li, Q., Gokel, G. W., and Gordon, J. I. (1992) J. Biol. Chem. 267, 7224–7239.

Doering, T. L., Raper, J., Buxbaum, L. U., Hart, G. W., and Englund, P. T. (1990) Methods 1, 288–296.

Doering, T. L., Raper, J., Buxbaum, L. U., Adams, S. P., Gordon, J. I., Hart, G. W., and Englund, P. T. (1991) Science 252, 1851–1854.

Doering, T. L., Pessin, M. S., Hoff, E. F., Hart, G. W., Raben, D. M., and Englund, P. T. (1993) J. Biol. Chem. 268, 9215–9222.

Duszenko, M., Ferguson, M. A. J., Lamont, G. S., Rifkin, N. R., and Cross, G. A. M. (1985) J. Exp. Med. 162, 1256–1263.

Englund, P. T. (1993) Annu. Rev. Biochem. 62, 121–138.

Gokel, G. W., Lu, T., Rudnick, D. A., Jackson-Machelski, E., and Gordon, J. I. (1992) Israel J. Chem. 32, 127–133.

Hamm, B., Schindler, A., Mecke, D., and Duszenko, M. (1990) Mol. Biochem. Parasitol. 40 (1), 13–22.

Heuckeroth, R. O., Glaser, L., and Gordon, J. I. (1988) Proc. Natl. Acad. Sci. USA 85, 8795–8799.

Heuckeroth, R. O., and Gordon, J. I. (1989) Proc. Natl. Acad. Sci. USA 86, 5262–5266.

Heuckeroth, R. O., Jackson-Machelski, E., Adams, S. P., Kishore, N. S., Huhn, M., Katoh, A., Lu, T., Gokel, G. W., and Gordon, J. I. (1990) J. Lipid Res. 31, 1121–1129.

Johnson, D. R., Cox, A. D., Solski, P. A., Devadas, B., Adams, S. P., Leimgruber, R. M., Heuckeroth, R. O., Buss, J. E., and Gordon, J. I. (1990) Proc. Natl. Acad. Sci. USA 87, 8511–8515.

Kishore, N. S., Lu, T., Knoll, L. J., Katoh, A., Rudnick, D. A., Mehta, P. P., Devadas, B., Huhn, M., Atwood, J. L., Adams, S. P., Gokel, G. W., and Gordon, J. I. (1991) J. Biol Chem. 266, 8835–8855.

Kishore, N. S., Wood, D. C., Mehta, P. P., Wade, A. C., Lu, T., Gokel, G. W., and Gordon, J. I. (1993) J. Biol. Chem. 268, 4889–4902.

Opperdoes, F. R. (1987) Annu. Rev. Microbiol. 41, 127–151.

Rapoport, L. and Neuman, M. S. (1947) J. Am. Chem. Soc. 69, 471–472.

Rudnick, D. A., Lu, T., Jackson-Machelski, E., Hernandez, J. C., Li, Q., Gokel, G. W., and Gordon, J. I. (1992) Proc. Natl. Acad. Sci. USA 89, 10507–10511.

Rudnick, D. A. McWherter, C. A., Gokel, G. W., and Gordon, J. I. (1993) Adv. Enzymol. 67, 375–430.

Zinsstag, J., Brun, R., and Gessler, M. (1991) Parasitol. Res. 77, 33–38.

What is claimed is:

1. A compound having the formula $$C_6H_5-CH=CH-(CH_2)_9-COOH.$$

* * * * *